(12) United States Patent
Niksa et al.

(10) Patent No.: US 7,541,004 B2
(45) Date of Patent: Jun. 2, 2009

(54) MEMS-BASED SENSOR FOR LUBRICANT ANALYSIS

(75) Inventors: Andrew J. Niksa, Chardon, OH (US); James D. Fousek, Brecksville, OH (US)

(73) Assignee: Predict, Inc., Cleveland, OH (US)

( * ) Notice: Subject to any disclaimer, the term of this patent is extended or adjusted under 35 U.S.C. 154(b) by 822 days.

(21) Appl. No.: 10/987,874

(22) Filed: Nov. 12, 2004

(65) Prior Publication Data

US 2006/0105467 A1 May 18, 2006

(51) Int. Cl.
*G01N 27/00* (2006.01)
*G01N 25/08* (2006.01)
*G01R 27/08* (2006.01)

(52) U.S. Cl. ............... 422/82.02; 436/150; 324/698
(58) Field of Classification Search ............ 422/82.01, 422/82.02; 436/150; 324/698
See application file for complete search history.

(56) References Cited

U.S. PATENT DOCUMENTS

| | | | |
|---|---|---|---|
| 3,233,173 A | 2/1966 | Lees et al. | |
| 4,047,814 A | 9/1977 | Westcott | |
| 4,058,766 A | 11/1977 | Vogel et al. | |
| 4,227,419 A | 10/1980 | Park | |
| 4,423,371 A | 12/1983 | Senturia et al. | |
| 4,629,334 A | 12/1986 | Hochstein | |
| 4,646,070 A | 2/1987 | Yasuhara et al. | |
| 4,689,553 A | 8/1987 | Haddox | |
| 4,733,556 A | 3/1988 | Meitzler et al. | |
| 5,025,222 A | 6/1991 | Scott et al. | |
| 5,045,798 A | 9/1991 | Hendrick | |
| 5,071,527 A | 12/1991 | Kauffman | |
| 5,103,181 A | 4/1992 | Gaisford et al. | |
| 5,196,898 A | 3/1993 | Tamura et al. | |
| 5,200,027 A | 4/1993 | Lee et al. | |
| 5,249,455 A * | 10/1993 | Cox ................... 73/61.44 |
| 5,260,665 A | 11/1993 | Goldberg et al. | |
| 5,262,732 A | 11/1993 | Dickert et al. | |
| 5,269,175 A | 12/1993 | Chmiel et al. | |
| 5,274,335 A | 12/1993 | Wang et al. | |
| 5,317,252 A | 5/1994 | Kranbuehl | |
| 5,334,941 A | 8/1994 | King | |
| 5,382,942 A | 1/1995 | Raffa et al. | |
| 5,457,396 A | 10/1995 | Mori et al. | |
| 5,504,573 A | 4/1996 | Cheiky-Zelina | |
| 5,521,515 A | 5/1996 | Campbell | |
| 5,540,086 A | 7/1996 | Park et al. | |
| 5,548,217 A | 8/1996 | Gibson et al. | |
| 5,596,266 A | 1/1997 | Mori et al. | |

(Continued)

OTHER PUBLICATIONS

Iotech Catalog, p. 65, Jan. 1995.

(Continued)

*Primary Examiner*—Lyle A. Alexander
*Assistant Examiner*—Dennis M White
(74) *Attorney, Agent, or Firm*—Ryan Kromholz & Manion S.C.

(57) ABSTRACT

A fluid contamination analyzer employs one or more MEMS-based sensors. The sensors are incorporated into probes or alternatively may be employed in an in-line analyzer residing in the fluid. The sensors, which can be selective to detect a distinct contaminant within the fluid, sense an impedance of the fluid, which is a function of its contamination and communicates the impedance to analysis circuitry.

27 Claims, 12 Drawing Sheets

U.S. PATENT DOCUMENTS

| | | |
|---|---|---|
| 5,604,441 A | 2/1997 | Freese, V et al. |
| 5,614,830 A | 3/1997 | Dickert et al. |
| 5,656,767 A | 8/1997 | Garvey, III et al. |
| 5,674,401 A | 10/1997 | Dickert et al. |
| 5,754,055 A | 5/1998 | McAdoo |
| 5,789,665 A | 8/1998 | Voelker et al. |
| 5,824,889 A | 10/1998 | Park et al. |
| 6,028,433 A | 2/2000 | Cheiky-Zelina et al. |
| 6,204,656 B1 | 3/2001 | Cheiky-Zelina et al. |
| 6,223,589 B1 | 5/2001 | Dickert et al. |
| 6,250,152 B1 | 6/2001 | Klein et al. |
| 6,253,601 B1 | 7/2001 | Wang et al. |
| 6,278,282 B1 | 8/2001 | Marszalek |
| 6,443,006 B1 | 9/2002 | Degrave |
| 6,449,580 B1 | 9/2002 | Bardetsky et al. |
| 6,459,995 B1 | 10/2002 | Collister |
| 6,509,749 B1 | 1/2003 | Buelna et al. |
| 6,513,368 B2 | 2/2003 | Bondarowicz et al. |
| 6,519,034 B1 | 2/2003 | Engler et al. |
| 6,535,001 B1 | 3/2003 | Wang |
| 6,553,812 B2 | 4/2003 | Park et al. |
| 6,557,396 B2 | 5/2003 | Ismail et al. |
| 6,564,126 B1 | 5/2003 | Lin et al. |

OTHER PUBLICATIONS

"Model 958PF On-Line Ferrograph", *Foxboro Analytical*, 1980, 4 pgs.

"958PF Series On-Line Ferrograph Installation and Operation", The Foxboro Company, 1980, 6 pgs.

"Journal Reprints", The British Institute of Non-Destructive Testing, M.H. Jones and A.R. Massoudi, Insight, vol. 37, No. 8, Aug. 1995, pp. 606-610.

"Basics of Measuring the Dielectric Properties of Materials", Hewlett Packard, 1992.

"The NIST 60-Millimeter Diameter Cylindrical Cavity Resonator: Performance Evaluation for Permittivity Measurements", Eric J. Vanzura, Richard G. Geyer and Michael D. Janezic, Aug. 1993, National Institute for Standards and Technology Technical Note.

"Advancement of PREDICT/DLI Industrial Sensors", M.A. Cheiky-Zelina, R.W. Brown and D.E. Schuele, Department of Physics, Case Western Reserve University, Mar. 1997.

\* cited by examiner

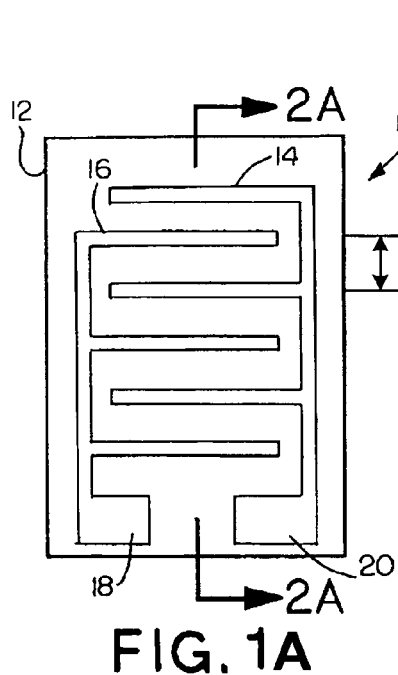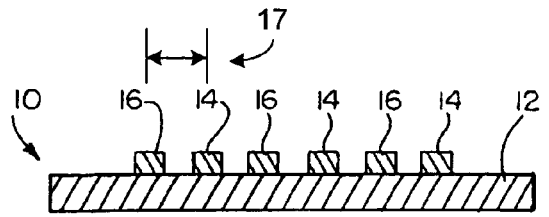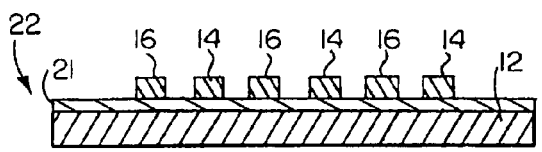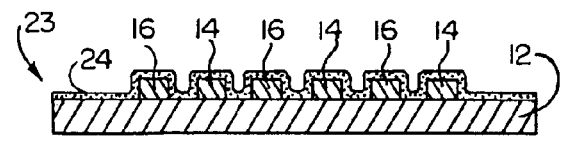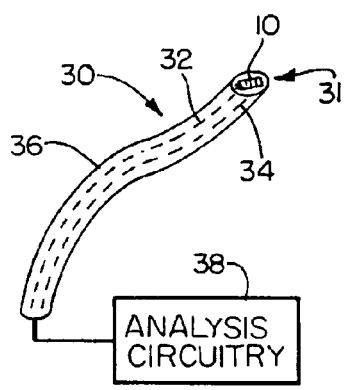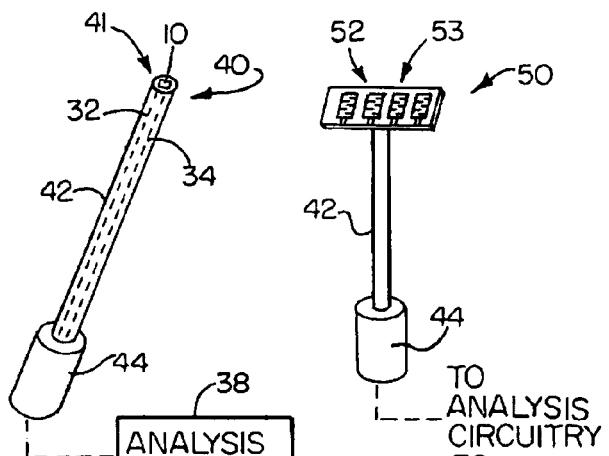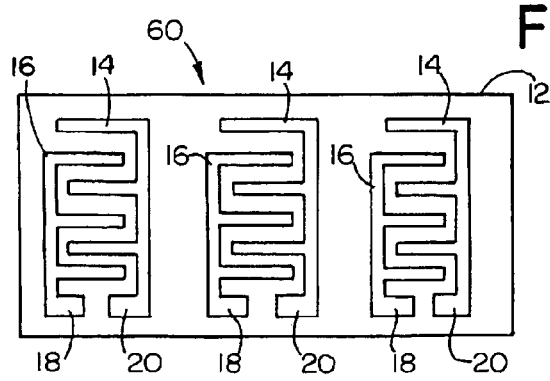

| Reference name | Real Component of Impedance | Reactive Component of Impedance | Reference Temperature | Temperature Compensation | DF | Fluid Property 1 |
|---|---|---|---|---|---|---|
| Oil 1 | R1 | I1 | T1 | C1 | DF1 | New |
| Oil 2 | R2 | I2 | T2 | C2 | DF2 | 90% life remaining |
| ••• | ••• | ••• | ••• | ••• | ••• | ••• |
| Oil n | Rn | In | Tn | Cn | DFn | 0% life remaining |

FIG. 17

MEMS-BASED SENSOR FOR LUBRICANT ANALYSIS

FIELD OF THE INVENTION

The present invention relates generally to an apparatus and method for analyzing fluids such as lubricants. More particularly, the invention relates to a miniature sensor using microelectromechanical (MEMS) device technology for detecting and monitoring conditions of a fluid, such as water content, oxidation and metallic or conductive particle contamination.

BACKGROUND OF THE INVENTION

The presence of corrosive products, contaminants, metallic particles, oxidation, etc. in fluids, such as lubricants, can cause problems. For example, contaminants in lubricants can lead to damage of machinery in which the lubricant is utilized, causing unnecessary or accelerated wear on the lubricated members.

Various approaches have been developed to detect conditions involving deterioration and/or contaminants in fluids. One conventional system described in U.S. Pat. No. 4,646,070 utilizes a pair of capacitor electrodes positioned in a fluid. The fluid serves as a dielectric between the electrodes to develop a frequency voltage signal across the capacitor electrodes. Based on such signal, the dielectric, and therefore, the deterioration of the fluid is determined. However, this solution suffers from a drawback in that the sensor is large and bulky and is difficult to move from machine to machine to make fluid contamination measurements.

U.S. Pat. No. 5,262,732 describes a system, which utilizes an oscillator circuit coupled to a capacitive sensor. The fluid under test is placed in a reservoir containing the capacitive sensor. The oscillator circuit generates a signal having a frequency that increases or decreases depending on the capacitance of the sensor. The system of U.S. Pat. No. 5,262,732 is also rather large and cumbersome and does not lend itself to portability. In the field, it would be difficult to transport the device from machine to machine to analyze the lubricant at the location of the machinery, for example.

Some prior art sensors have been rather large so that a user could insert the sensor into the fluid and thereby remove a fluid sample from a machine for analysis. This large, sturdy construction also allowed the sensor to be subsequently cleaned for use at another machine without causing damage to the sensor. Unfortunately, in some machines, obtaining a manual fluid sample with a large, unwieldy sensor is inconvenient due to machine construction. Also, in some applications, it is desirable to affix a lubricant analysis sensor to the machine in the lubricant fluid flow path (called an in-line configuration) in order that a user may merely attend the machine and obtain a lubricant contamination reading without having to insert an analyzer apparatus into the fluid flow path. In some cases, prior art sensors are too large and unwieldy and do not conveniently affix to the machine without interfering with proper machine operation.

As disclosed in U.S. Pat. Nos. 4,047,814 and 5,504,573, magnetic field gradients have been utilized to precipitate conductive or ferromagnetic particulates out of a sample fluid (e.g., a lubricant) such that particulates of varying sizes are withdrawn along a horizontal strip for subsequent analysis. Knowledge of the particulate size distribution is then utilized to determine the status of machinery wear and the potential for failures from wearing parts, etc. Prior to U.S. Pat. Nos. 4,047,814 and 5,504,573, this method relied upon a visual analysis of particulate distribution, which was a strong function of the technician's experience performing the analysis, thereby leading to inconsistent conclusions. In addition, since the horizontal strip was removed for analysis, evaluation of the fluid at the machine site was difficult and, in many cases, impossible.

U.S. Pat. Nos. 4,047,814 and 5,504,573 provided analysis improvement over the manual analysis by illuminating the particulate distribution with radiation and detecting the radiation via a plurality of photodetectors that traverse the particulate sample. Although such a technique provides for an improvement in subsequent analysis conclusions, this technique does not overcome the requirement that an operator initially procure the sample and send it off-site for analysis. The sample must still be removed for analysis which limits the locations in which such analysis materials may be located and, in some cases, prohibits their use altogether. Further, if one wishes to affix the particulate distribution collection apparatus with its analysis equipment so that the horizontal strip need not be removed from the machine, the radiation source and photodetectors are undesirably large and thereby further limit the scope of their application.

A miniature sensor for lubricant analysis was disclosed in commonly owned U.S. Pat. No. 6,204,656. The sensor included one or more micro-miniature sensors that provided a substantial reduction in sensor dimensions relative to prior art sensors. The sensors are incorporated into probes for easy lubricant fluid accessibility or in an in-line configuration. The sensors sense a capacitance of the fluid (therefore the impedance), and based on the impedance, determine the condition of the fluid. The sensor disclosed in U.S. Pat. No. 6,204,656, however, determined the impedance of the fluid based on the magnitude of the impedance and contaminant selective materials were not thoroughly discussed.

In view of the aforementioned shortcomings associated with existing systems for analyzing conditions of a fluid such as a lubricant, there is a strong need in the art for a fluid screening device which provides detailed information regarding the particular types of contamination, degree of oxidation or other deterioration, etc. Moreover, there is a strong need in the art for such a screening device which is miniature and thereby provides for ease of lubricant contamination status procurement for machine predictive maintenance programs.

SUMMARY OF THE INVENTION

According to one aspect of the invention, a fluid contamination analyzer includes at least one sensor. The at least one sensor includes: a substrate; a plurality of electrodes formed over the substrate; and a contaminant selective layer disposed adjacent at least one of (i) the electrodes and (ii) the substrate, said layer being selective to attract a predetermined contaminant within the fluid; wherein when a fluid contacts the sensor an impedance of the fluid may be determined using the electrodes of the sensor, thereby providing an indication of fluid contamination.

Another aspect of the invention relates to an in-line fluid contamination analyzer, including: an array of MEMS-based sensors located within a fluid, wherein each sensor includes a substrate, a plurality of electrodes formed over the substrate, and a contaminant-selective layer disposed adjacent the electrodes, said array including: a first MEMS-based sensor having a first contaminant-selective layer which is selective to attract a first class of contaminant within the fluid; a second MEMS-based sensor having a second contaminant-selective layer which is selective to attract a second class of contaminant within the fluid; and a third MEMS-based sensor having a third contaminant-selective layer which is selective to attract a third class of contaminant within the fluid; wherein each sensor is operative to determine an impedance of the fluid contacting each sensor, thereby providing an indication of fluid contamination.

Yet another aspect of the invention relates to a fluid contamination analyzer, including: a first reference MEMS-based sensor disposed within a reference housing, said reference housing containing a substantially contaminant-free volume of the fluid being analyzed; and a plurality of sample MEMS-based sensors disposed adjacent the reference housing within a fluid.

Another aspect of the invention relates to a fluid contamination analyzer, including at least one MEMS-based sensor, said at least one sensor including: a substrate; a plurality of conductors formed over the substrate; and a local heater disposed adjacent the at least one MEMS-based sensor, said local heater providing a temperature gradient through which the fluid is run; wherein the conductors form electrodes of the sensor and when a fluid contacts the sensor an impedance of the fluid may be determined as a function of temperature, thereby providing an indication of fluid contamination.

Yet another aspect of the invention relates to a method of analyzing the quality of a fluid, including the steps of: immersing a sensor into the fluid, wherein the fluid acts as a dielectric for the sensor; obtaining a complex impedance of the fluid; measuring a temperature of the fluid in contact with the sensor; applying a correction factor to the complex impedance based on the measured temperature of the fluid; and estimating the quality of the fluid based on a comparison of known fluids producing substantially the same Dissipation Factor and complex impedance values.

Another aspect of the invention relates to a method of analyzing the quality of a fluid, including the steps of: immersing a sensor into the fluid, wherein the fluid acts as a dielectric for the sensor; measuring an impedance of the fluid over a temperature gradient; and estimating the quality of the fluid based on a change in slope of the measured impedance over the temperature gradient.

Yet another aspect of the invention relates to a method of analyzing the quality of a fluid in which a sensor has been immersed, wherein the fluid acts as a dielectric on the sensor, including the steps of: using a contaminant selective layer on the sensor to selectively attract contaminants within the fluid near a surface of the sensor; measuring an impedance of the fluid near the surface of the sensor; and correlating the quality of the fluid to the measured impedance of the fluid.

Another aspect of the invention relates to a method of analyzing the quality of a sample fluid, wherein the fluid acts as a dielectric on the sensor, comprising the steps of: immersing a sample sensor in the sample fluid; immersing a reference sensor in a substantially contaminant-free reference fluid, wherein the reference fluid and the sample fluid are the same type of fluid; measuring an impedance of the fluid near the surface of the sample sensor and the reference sensor; and correlating the quality of the sample fluid to the measured impedance of the sample fluid and the reference fluid.

Other aspects, features, and advantages of the invention will become apparent from the following detailed description. It should be understood, however, that the detailed description and specific examples, while indicating several embodiments of the present invention, are given by way of illustration only and various modifications may naturally be performed without deviating from the present invention.

BRIEF DESCRIPTION OF THE DRAWINGS

FIG. 1A is a top view of a MEMS-based sensor according to an embodiment of the invention.

FIG. 2A is a cross section diagram illustrating the MEMS-based sensor of FIG. 1A taken along arrows 2A-2A.

FIG. 2B is a cross section diagram illustrating an alternative MEMS-based sensor according to the invention.

FIG. 2C is a cross section diagram illustrating another alternative MEMS-based sensor according to the invention.

FIG. 3A is a diagram illustrating use of the MEMS-based sensor of FIG. 1A in an elongate probe.

FIG. 3B is a diagram illustrating use of the MEMS-based sensor in a rigid, elongate probe having a handle.

FIG. 3C is a diagram illustrating a MEMS-based sensor array at one end of a probe.

FIG. 4 is a top view illustrating an array of MEMS-based sensors as disclosed in FIG. 1A.

FIG. 17 is an exemplary database structure used to store fluid sample data in accordance with an embodiment of the present invention

DETAILED DESCRIPTION OF THE INVENTION

Figure 1B:
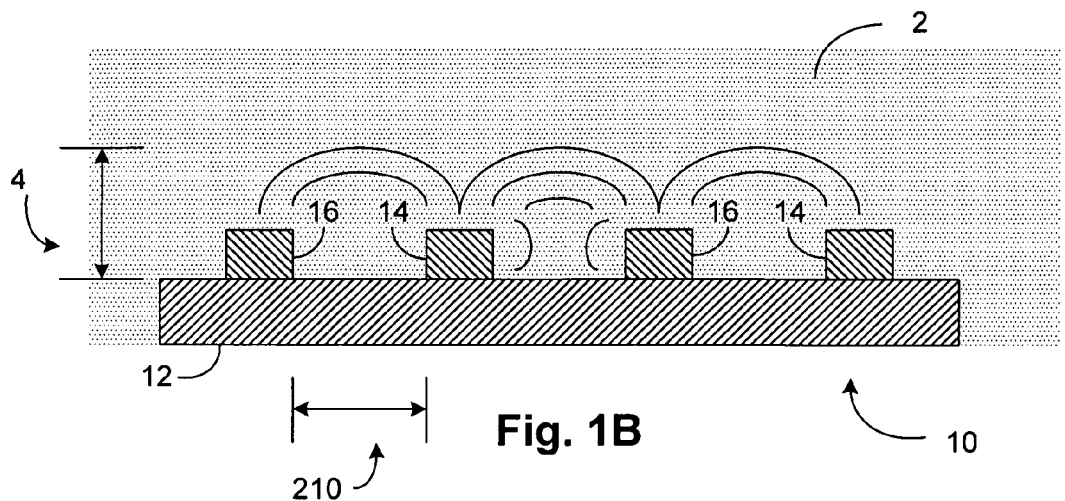
FIG. 1B is a cross section diagram illustrating the field of view of the MEMS-based sensor of FIG. 1A

The present invention will now be described with reference to the drawings wherein like reference numerals are used to refer to like elements throughout. As will become more apparent based on the following description, a fluid contamination analyzer for monitoring contaminants in lubricating fluids utilizes micro-electromechanical (MEMS)-based sensors, thereby substantially reducing the sensor dimensions while providing a similar electrical response. This results in a greater variety of machine fluid analysis applications for the sensor. The MEMS-based sensor fabrication techniques also allow for a substantial reduction in sensor costs and provide high sensor manufacturability. Such fabrication techniques also allow for a substantial number of sensor variations with a sensor array for collecting a variety of types of data relating to fluid contamination.

Throughout the disclosure, reference will be made to impedance and impedance measurements. Impedance can be represented and analyzed in many forms, and each are contemplated to fall within the scope of the present invention. For example, impedance may be characterized as capacitance, complex capacitance, resistance and reactance, capacitance and dissipation factor, impedance and phase angle, admittance, susceptance and conductance. Each of these characterizations have their own terminologies. For example, for capacitance the terms capacitance, dissipation factor, Tan delta, Q factor or loss factor may be utilized.

Additionally, the invention will be described with respect to an in-line sensor. However, the sensor can be applied in other configurations and/or applications, and the description with respect to an in-line sensor is not intended to be limiting in any way. Other configurations include, for example, placement of the sensor in a sump (e.g., not in a direct path of fluid flow) or external from the fluid flow (e.g., a separate test unit not part of the machine).

FIG. 1A is a top view of a MEMS-based sensor 10 formed using MEMS device fabrication techniques. The sensor 10 includes a substrate 12, preferably made of glass or quartz, upon which a conductive layer is formed and etched to create a pair of interdigitated conductors 14 and 16, respectively. The first conductor 14 forms a first electrode 14 while the second conductor 16 forms a second electrode 16. The electrodes are interdigitated to provide uniformity in impedance measurement. Alternatively, the electrodes may take on any suitable configuration and still fall within the scope of the invention. The electrodes 14, 16 can be less than 1 micron wide, the limiting factor being the ability to manufacture the thin electrodes and the conductivity of the material. There is no particular constraint on the upper limit of the electrode width. In one embodiment, the electrodes have a width between about 1 micron and about 50 microns.

In another embodiment, the substrate 12 can be made of ceramic or a semiconductor material, such as silicon, silicon nitride, silicon carbide, germanium and the like. As is discussed more fully below, the substrate material may be chosen to provide an optimized selectivity with respect to one or more contaminants being detected.

In yet another embodiment, the interdigitated electrodes 14, 16 are formed of tungsten, platinum, gold, chrome, aluminum, polysilicon, titanium, nickel, copper, silver, and the like. Electrodes 14 and 16 are electrically isolated from one another and may be coupled to either discrete instrumentation or circuits integrated with the substrate 12 or other integrated circuits via bond pads 18 and 20, respectively. Since the sensor 10 is fabricated using conventional MEMS-based and/or semiconductor processing techniques, fine line width geometries may be constructed thereby allowing the sensor dimensions to be 1 mm by 1 mm or smaller. MEMS-based techniques allow the sensor to be reduced in size while maintaining a relatively large feedback signal and, therefore, achieving good precision of the measured data.

During operation, the sensor analyzes a thin film of material, e.g., a fluid, directly adjacent to the sensor surface. In other words, an electric field of the sensor 10 extends up into the fluid at least a distance equal to about the line spacing 17 (i.e., the distance of separation between adjacent electrodes) of the electrodes 14, 16 and generally a distance significantly further. For example, and with further reference to FIG. 1B, if the line spacing 17 were 10 microns, then the sensor 10 could analyze or "look into" the fluid 2 a distance 4 of at least 10 microns above the surface of the sensor 10. Similarly, if the line spacing were 100 microns, then the sensor 10 could analyze the fluid at least 100 microns above the surface of the sensor 10. The line spacing 17 of the electrodes 14, 16 can be less than 1 micron or up to about 250 microns, for example. In one embodiment, the line spacing of the electrodes 14, 16 is 1 micron wide and equally spaced (e.g., the line spacing 17 is 1 micron), and in another embodiment the line spacing is about 2 microns and equally spaced. As will be appreciated, the line spacing 17 may be larger or smaller as desired.

The sensor 10 operates in the following manner. When the sensor 10 comes into contact with a fluid sample, the fluid acts as a dielectric between the electrodes 14, 16 thereby impacting the impedance of the sensor. By way of example, the sensor can be approximated by a parallel plate capacitor having a capacitance characterized by $C = \in A/d$, wherein A is the electrode surface area and d represents the electrode spacing. The measured capacitance provides an indication of the properties of the dielectric (the fluid). Accordingly, the sensor 10 senses the capacitance (and therefore the impedance) of the fluid at its leads (bond pads 18 and 20) and provides this value at the bond pads 18 and 20 for analysis by analysis circuitry (not shown). The analysis circuitry takes the impedance value and determines the level of fluid contamination based upon a comparison with 1) a known clean fluid sample; 2) an expected or reference value; or 3) by trending, e.g., looking at a change over time of a capacitance, a phase angle, resistance, dielectric, etc. Various methods exist for analyzing fluid contamination. At least one method contemplated by the present invention includes using the sensed fluid impedance as a component within an oscillator circuit, thereby impacting the circuit's oscillating frequency which may be used to determine the level of fluid contamination. This method is disclosed in detail in co-owned U.S. Pat. No. 6,028,433 entitled "Portable Fluid Screening Device and Method," which is hereby incorporated by reference in its entirety.

It is to be appreciated that impedance is generally measured. Therefore, the term sensor "impedance" will be used in the remainder of this disclosure. It should be noted that although the capacitance of the fluid is analyzed through the impedance, the impedance sensor 10 extends to other fluid impedance variations and therefore, for example, contemplates inductive type sensors within the scope of the present invention.

Turning now to FIG. 2A, a cross sectional view of the sensor 10 taken along lines 2A-2A of FIG. 1A is illustrated. The sensor 10 has the electrodes 14 and 16 located along a horizontal plane on the substrate 12. When a lubricant fluid sample contacts the sensor 10, it rests between and/or above the electrodes 14 and 16, thereby affecting the dielectric constant therebetween. Accordingly, the presence of contaminants within the fluid results in different impedance readings of the sensor at its leads (bond pads 18 and 20). These differences are analyzed via analysis circuitry (not shown) to determine, within an acceptable accuracy bandwidth, the level of fluid contamination, which may then be used, for example, either as an indication for timely fluid replacement or an indication of machine wear for preventative maintenance and/or quality control purposes.

Although the electrodes 14 and 16 are illustrated in FIG. 2A as residing entirely within a single horizontal plane, it should be understood that the substrate 12 may undertake a variety of contours and the electrodes 14 and 16 may follow that contour to be customized for various applications as may be desired. Each of these sensor variations are contemplated by the present invention. In an alternate embodiment, illustrated in FIG. 2B, the sensor 22 includes insulating layer 21, such as silicon nitride, between the substrate 12 and the electrodes 14 and 16. As is described more fully below, the insulating layer 22 serves a variety of purposes, including, but not limited to, electrically insulating the electrodes 14 and 16 from an electrically conductive substrate 12, providing a sensor that can operate at higher operating temperatures, and enhancing selectivity of the sensor with respect to detecting a particular contaminant within the fluid under test.

FIG. 2C is a cross-sectional view of an alternative embodiment of a sensor 23 similar to the sensor 10 of FIG. 1A. Sensor 23 includes the substrate 12 having the electrodes 14 and 16 formed thereon. Subsequently, an insulating layer 24, such as silicon dioxide layer, is formed over the electrodes 14 and 16 which helps protect the sensor 23 from experiencing "shorts" across the electrodes 14 and 16 caused, for example, by substantially sized conductive particulates in a fluid under test. The insulated sensor 23 provides improved performance in detection of non-particulate forms of contamination, for example, water content in the fluid or fluid oxidation. Additionally, and as will be described in more detail below, the insulation layer 24 can be selected to enhance the selectivity of the sensor with respect to detecting a particular contaminant within the fluid under test or to prevent accumulation of soils or contaminants on the sensor surface.

As stated above, the sensors 10, 22 and 23 of FIGS. 2A, 2B and 2C substantially reduce the dimensions of a fluid sensor from approximately 2 in.×2 in. to approximately 1 mm×1 mm, thereby providing substantial improvements in procuring fluid samples for analysis. For example, a probe utilizing a sensor having such dimensions may easily be inserted into a machine containing a fluid for analysis without either substantially impacting the machine's operation or requiring any disassembly of the machine. FIG. 3A illustrates a probe assembly 30 incorporating the sensor at one end 31. The bond pads 18 and 20 (not shown) of the sensor 10 are coupled to lines 32 and 34 along a flexible probe body 36, thereby transmitting the fluid impedance sensed by the sensor 10 to an analysis circuit 38. The flexible, elongate probe body 36 allows a user to manipulate the probe into numerous shapes to access difficult-to-reach fluid samples within operating machinery. Further, since the sensor 10 is compact in size, the sensor 10 does not negatively impact the size of the probe 30 at the end 31, thereby facilitating the testing of fluid samples in difficult-to-reach locations without adversely impacting a machine's operation or requiring a disassembly of the machine.

In FIG. 3A, the analysis circuitry 38 is illustrated as being separate from the probe. Alternatively, the analysis circuitry may reside at the end 31 of the probe 30 as a circuit integrated with the sensor 10. This alternative embodiment advantageously provides for fluid contamination level determinations to be made local to the measurement site itself, thereby improving analysis accuracy by eliminating errors due to electrical line losses and noise.

FIG. 3B, much like FIG. 3A, is a diagram illustrating an alternative probe assembly 40 having a sensor 10 at one end 41. The sensor 10 is connected to lines 32 and 34 via bond pads 18 and 20 (not shown), which extend through a substantially rigid channel member 42 to a handle 44. The handle 44 provides for ease of use and connects the lines 32 and 34 to the analysis circuitry 38. Alternatively, handle 44 may contain a communications circuit therein to provide wireless transmission of the fluid impedance data to the analysis circuitry 38 through an RF data link, for example. Such wireless capability provides even greater flexibility by allowing a user to be unimpeded by any wire length, etc., which is useful and safe in a factory setting utilizing heavy machinery having moving parts. Although the rigid channel member 42 is not as ductile as the elongate body 36 of FIG. 2A, the channel member 42 provides for firm, precise positional control of the sensor location, while the handle 44 allows a user to easily manipulate the probe assembly 40 while avoiding hazards present by moving parts within the machinery.

Another advantage provided by the dimensional feature of the sensor 10 is that an array of such sensors may be incorporated together within a single probe assembly without substantially impacting the probe size. FIG. 3C illustrates such a probe assembly 50 wherein an array 52 of sensors reside at one end 53 of the probe assembly 50. It is to be appreciated that FIG. 3C greatly exaggerates the dimensions of the array 52 with respect to the other members in order to illustrate the array 52 of sensors 10. In actual practice, the sensor array 52 can reside at the end 53 of the probe assembly 50 and not be substantially larger than the channel member 42, for example. In one embodiment, the sensor array 52 may be utilized to provide improved analysis accuracy by providing impedance measurement redundancy. For example, since a fluid contamination concentration is not always uniform (such as when a substantially large particulate is identified, which skews the aggregate contamination determination), the sensor array 52 allows for multiple fluid impedance readings to be collected and subsequent data processing techniques used to interpret the data to accurately determine the fluid contamination level. For example, multiple readings may be averaged together or if one reading is substantially different from the others, it may be ignored. Alternatively, various statistical operations may be performed on the collected data to yield a more accurate determination of fluid contamination. When utilizing an array 52 as illustrated in FIG. 3C, each sensor 10 at the probe end 53 may be individually hard-wired to analysis circuitry 38 via the channel member 42 and handle 44. Alternatively, a time multiplexer circuit (or other type multiplexing methodology) may be utilized at the end 53 of the probe assembly 50 to reduce the need for multiple lines 32 and 34 in the channel member 42 to thereby keep the probe assembly 50 compact.

The sensor array 52 of FIG. 3C may comprise various configurations. In one embodiment, multiple sensors 10 may be formed on a single substrate 12, such as the array 60 illustrated in FIG. 4. In one embodiment, multiplexing circuitry may be integrated onto the substrate 12 to collect the multiple measured fluid impedances and multiplex them (via either time multiplexing or other multiplexing technique) for transmission via lines 32 and 34 to the analysis circuitry 38. Further still, the analysis circuitry 38 may also be integrated onto the substrate 12 such that data acquisition and fluid contamination determination may be made at the end 53 of the probe assembly 50, thereby reducing fluid determination errors due to line loss, noise, etc. Alternatively, multiple discrete sensors 10 having separate substrates 12 may reside on another support structure and be affixed to the end 53 of the probe assembly 50.

The sensor arrays 52 and 60 of FIGS. 3C and 4 may comprise various array configurations as may be desired. For example, as illustrated, the sensor array 52 may be configured in a longitudinal row or be stacked vertically. In addition, the sensor array 52 may extend into two dimensions to form a square shaped sensor or any type of pattern depending upon the desired application. In yet another alternative embodiment, the sensor array may extend into three dimensions by stacking the sensors above one another such that sufficient space is provided for fluid contact to the various sensors. Any configuration of sensors 10 to form one dimensional, two dimensional or three dimensional arrays are contemplated by the present invention.

Figure 5:
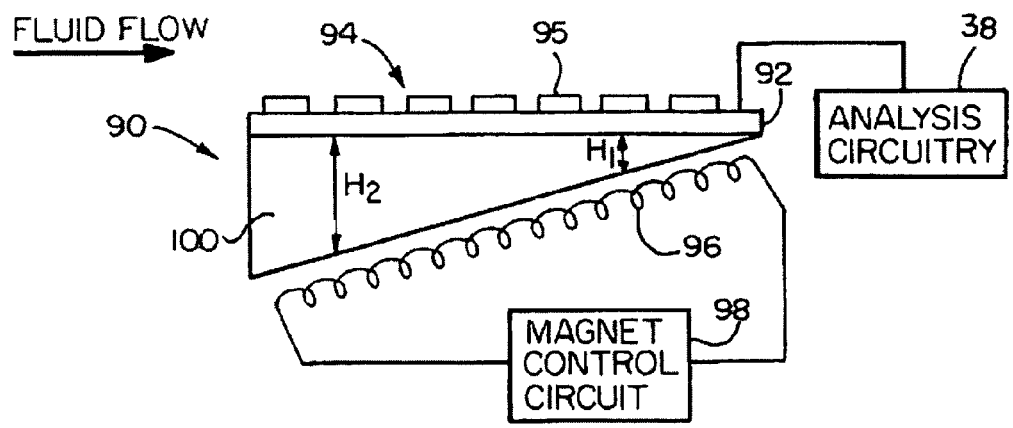
FIG. 5 is a side view of a system according to one aspect of the invention having an array of MEMS-based sensors placed within a magnetic field intensity gradient.

FIG. 5 is a system level diagram which illustrates a fluid contamination analyzer system 90 having a substrate 92 upon which a sensor array 94 resides, wherein each sensor 95 is constructed and behaves as the sensors 10, 22 and 23 of FIGS. 2A, 2B and 2C, respectively. Each sensor 95 is coupled (not shown) to the analysis circuitry 38 either directly or via a multiplexer circuit that may reside on the substrate 92. A magnetic field source 96, preferably an electromagnet coil or a movable permanent magnet, is coupled to a magnetic control circuit 98 to selectively activate the magnetic field source 96, such that the magnetic field may be turned on and off as desired. The magnetic field source 96 is preferably oriented to provide a magnetic field intensity gradient along a length of the sensor array 94. Preferably, the orientation is determined by a spacer wedge 100, as illustrated, however, other mechanisms such as brackets, etc. may also be utilized and are contemplated by the present invention.

The sensor array 94 of FIG. 5 operates in the following manner. A lubricant fluid for analysis is brought into contact with the sensor array 94. This may be accomplished by either placing the fluid contamination analyzer system 90 on a probe and inserting the sensor array 94 into the fluid or preferably affixing the system 90 to a machine in the fluid flow path to thereby provide an in-line fluid analyzer. In another embodiment, the fluid may be removed from the machine and brought into contact with the sensor array 94. The magnetic control circuit 98 activates the coil 96, thereby generating a magnetic field. The sensor array 94, due to its positional orientation with respect to the coil 96, experiences a magnetic field intensity gradient along its length such that at one end a large magnetic field intensity ($H_1$) is experienced at the substrate 92, while at another end a substantially smaller magnetic field intensity ($H_2$) is experienced at the substrate 92. Due to the magnetic field intensity gradient, ferromagnetic particles (contaminants) of differing sizes in the fluid are distilled from the fluid flow path onto the sensor array 94, such that a particulate distribution is generated across the sensor array 94. Therefore, each sensor 95 in the sensor array 94 will have a unique impedance due to the size and quantity of the particulates at that location. This impedance information is then used by the associated analysis circuitry 38 and processors to determine how much contamination exists at differing particulate sizes, which may be utilized to determine wear modes, wear trends, etc. After the impedance data has been collected, the magnetic control circuit 98 deactivates the coil 96 or moves the permanent magnet away, thereby turning the magnetic field off. Without any magnetic field acting on the particles, the force of fluid flow substantially removes particles from the sensor array 94.

Various modifications and alternative embodiments may be employed with the sensor array 94. In one alternative embodiment, a magnetic field intensity gradient may be achieved by utilizing a plurality of independent magnetic field sources fixed at varying distances from the substrate 92 or wherein each source has a unique magnetic field intensity such that their aggregation provides a magnetic field intensity gradient. Any type of magnetic field source or configuration of sources that would provide a variable magnetic field intensity across the sensor array 94 is contemplated in the present invention. Furthermore, although a coil is the preferred magnetic field source 96, any other type of magnetic source falls within the scope of the present invention.

Figure 6:
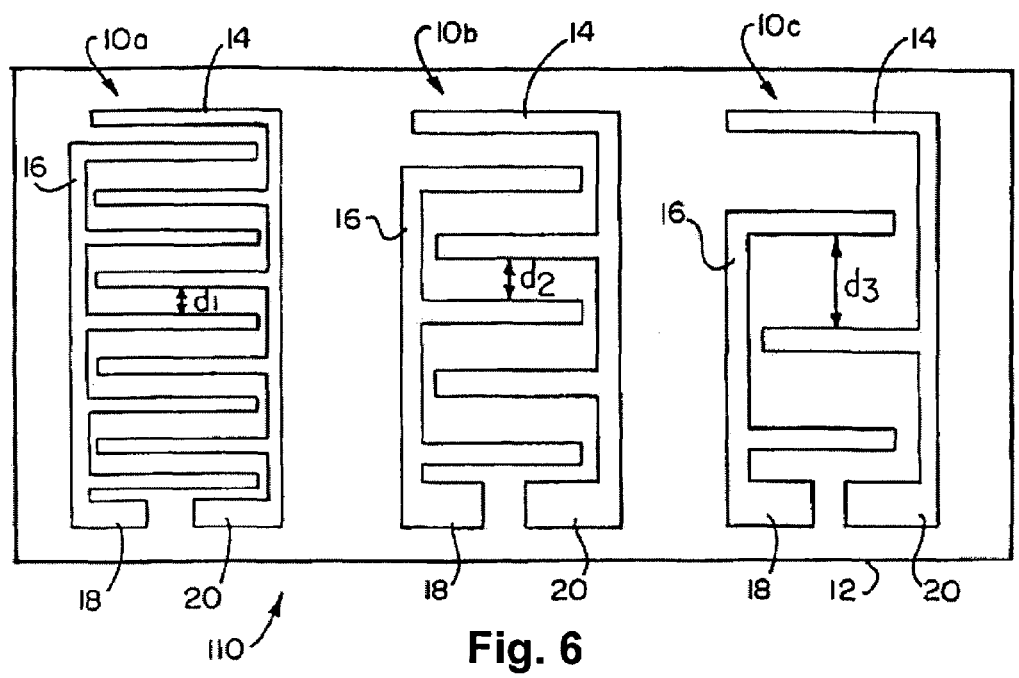
FIG. 6 is a top view of an alternative embodiment of the invention, wherein an array of MEMS-based sensors have variations in electrode spacings.

Another embodiment is illustrated in FIG. 6. FIG. 6 is a top view of a sensor array 110 wherein a substrate 12 contains a plurality of sensors 10 formed thereon. Each sensor 10 is much like the sensor of FIG. 1A (or alternatively sensors 22 or 23 of FIGS. 2B and 2C), having a substrate 12, conductors (electrodes) 14 and 16 and bond pads 18 and 20. The sensor array 110 differs from the sensor array 60 of FIG. 4 in that at least one of the sensors varies from the others with respect to the spacing between the interdigitated electrodes. For example, as illustrated in FIG. 6, sensor 10a has a somewhat close conductor spacing ($d_1$) for fine-sized particulates, sensor 10b has a larger electrode spacing ($d_2$) for medium-sized particulates and sensor 10c has a relatively larger electrode spacing ($d_3$) to accommodate large-sized particulates (wherein $d_1 < d_2 < d_3$). Such a variable electrode spacing sensor array 110 further accommodates particulate contamination distribution determinations by helping to delineate the size of the particulates due to the difference in spacing of the electrodes 14 and 16. Therefore to carry out this feature, the sensor 10c is preferably located within the array 110 near the largest magnetic field intensity which has sufficient strength to distill large-sized contaminants from the fluid, while sensor 10a preferably is located within the array 110 near the weakest magnetic field intensity which has sufficient strength to distill small-sized contaminants from the fluid.

Figure 7:
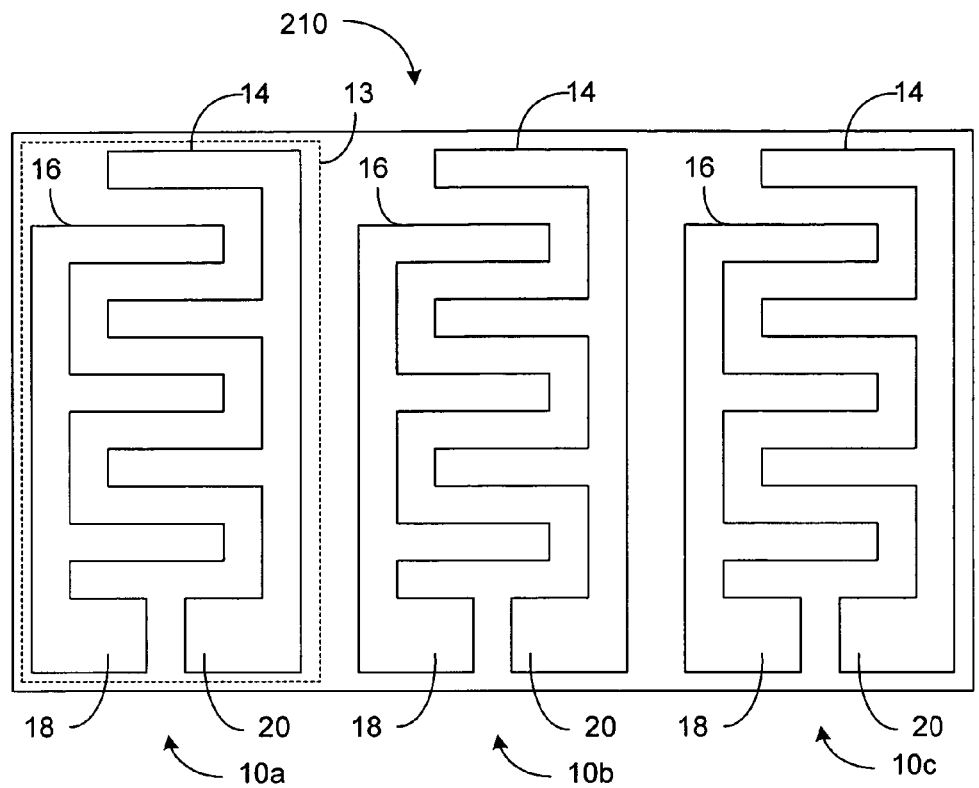
FIG. 7 is a top schematic view of an alternative embodiment of the invention, wherein an array of MEMS-based sensors includes a reference sensor.

With reference now to FIG. 7, a sensor array 210 includes a substrate 12 and a plurality of sensors 10a, 10b, 10c formed thereon. Each sensor includes a substrate 12, a pair of electrodes 14 and 16 and associated bond pads 18 and 20. In one embodiment, a first sensor 10a serves as a reference sensor, while the other sensors 10b, 10c are sample sensors for detecting one or more fluid contaminants, including, but not limited to, particles, water, acid, and the like.

Figure 8:
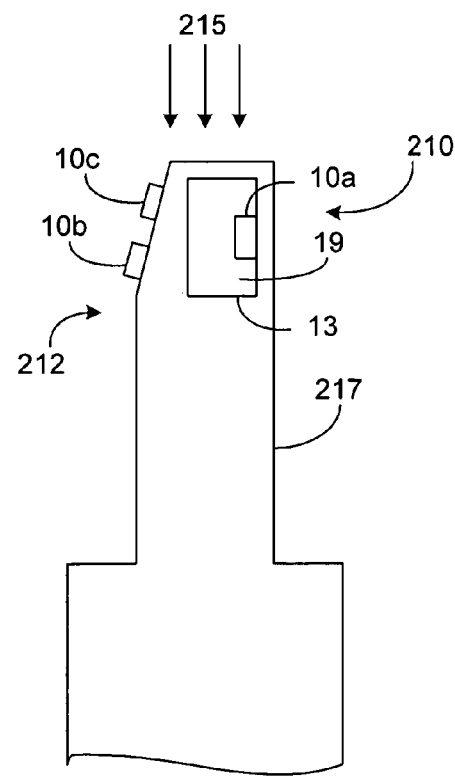
FIG. 8 is a sectional view illustrating an array of MEMS-based sensors including a reference sensor, wherein the MEMS based sensors are mounted on a probe.

In one embodiment, illustrated in FIG. 8, a sensor assembly 212 includes the sensor array 210 and a sensor housing 217. As shown, the reference sensor 10a is exposed or otherwise subjected to a known reference fluid 19, within the reference housing 13, having a composition and purity, which remains relatively fixed. For example, in a machine which employs a lubrication or cooling oil (flowing in a direction along arrows 215), the reference sensor 10a may be contained or otherwise housed in a reference housing 13, which is disposed adjacent the sample sensors 10b, 10c. In one embodiment, the reference housing 13 is comprised of a thermally conductive material, such that the temperature of the reference fluid 19 within the reference housing 13 is at approximately the same temperature as the fluid circulating throughout the machine.

Figure 13:
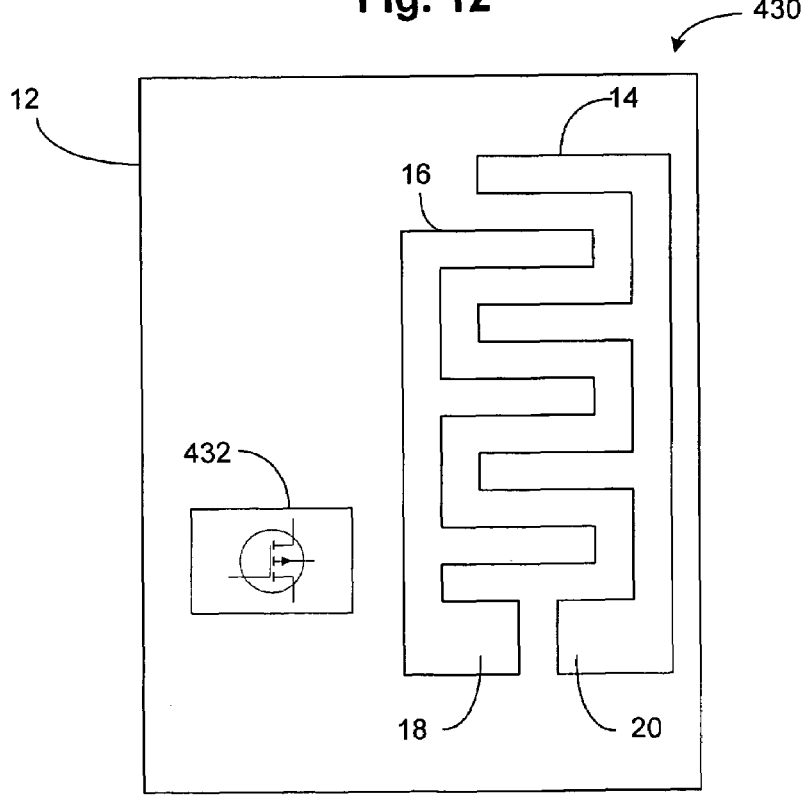
FIG. 13 is a top view of an alternative embodiment of the invention, wherein the MEMS based sensor includes a non-volatile memory device.

Preferably, the reference sensor 10a is immersed in or otherwise exposed to "clean" oil, i.e., oil which is not circulated throughout the machine and is not readily exposed to contamination. In this embodiment, the reference sensor is exposed to a reference oil having the same composition as the oil circulated throughout the machine. In addition, the reference oil and associated reference sensor 10a are subjected to all of the same conditions as the circulated oil and associated sample sensors 10b, 10c, except for the contaminants which develop in the circulated oil over time. As such, the capacitance readings from sample sensors 10b, 10c can be compared to the capacitance reading from reference sensor 10a in order to determine changes (e.g., the development and or presence of contaminants) in the circulated sample oil, and thereby providing enhanced accuracy. It is to be appreciated that the sensor assembly 212 of FIG. 8 may be used in conjunction with a probe, such as those illustrated in FIGS. 3A-3C, as well as in an in-line configuration (as illustrated in FIG. 13). It is to be appreciated that the reference housing 13 may be removable in order for the reference fluid 19 contained therein to be changed periodically.

Figure 9A:
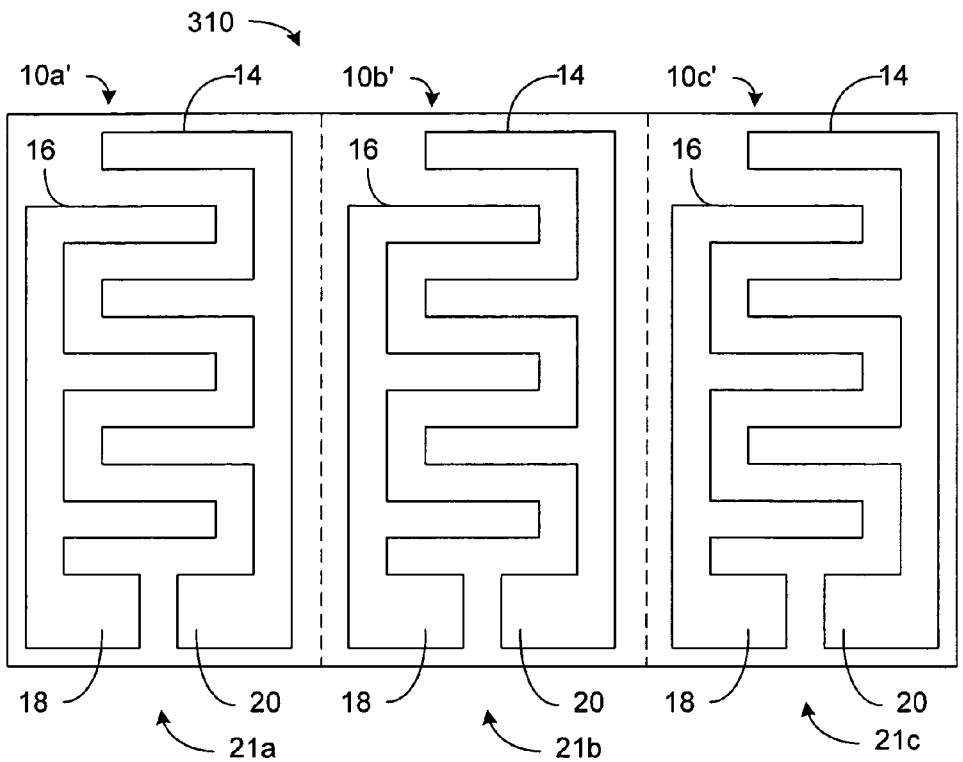
FIG. 9A is a top view of an alternative embodiment of the invention, wherein an array of MEMS-based sensors include a selective layer to detect particular contaminants, wherein the selective layer is formed between the electrodes and the substrate.

With reference to FIG. 9A and continued reference to FIGS. 1-4, in another alternative embodiment, a sensor array 310 includes a substrate 12 and a plurality of sensors 10a', 10b', 10c' formed thereon. Preferably, each sensor 10a', 10b', 10c' is sensitive to or otherwise selective of a particular fluid contaminant. More particularly, each sensor 10a', 10b', 10c' can include a different contaminant-selective layer. For example, the contaminant-selective layer can include an insulating or intermediate layer 21a, 21b, 21c, disposed between the electrodes 14, 16 and the substrate 12, as shown in FIG. 2B. Each intermediate layer 21a, 21b, 21c is chosen in order to provide a surface to which a fluid containing a contaminant of interest would preferentially adhere, thereby providing a stronger impedance measurement of the presence of the particular contaminant of interest within the fluid.

For example, an intermediate layer comprised of glass would be particularly sensitive to water within the fluid, while an intermediate layer comprised of silicon nitride would be particularly sensitive to soot and oxidation within the fluid. The sensitivity of a particular contaminant selective layer with respect to a particular contaminant can be determined empirically. The contaminant selective layer can be formed from silicon nitride, silicon dioxide, cerium dioxide, glass, quartz, aluminum oxide, aluminum nitride, boron nitride, titanium nitride, gallium nitride, diamond, diamond like carbon and silicon carbide. Hydrophilic materials provide more sensitivity to water, while hydrophobic materials provide less sensitivity to water.

According to one embodiment, the contaminant selective layer is formed from organic coatings, such as parylene, epoxy, polyimide, polycarbonate, polyester, polyphenylene sulfide, and the like.

According to another embodiment, the contaminant selective layer is formed from a low-K material or stack of materials to form a low-K dielectric stack. As used herein, a "low-K material" or a "low-K dielectric material" refers to a material, or stack of materials, having a relative permittivity in one embodiment of about 5 or less, and in another embodiment of about 3 or less. Relative permittivity is the ratio of the absolute permittivity ($\in$) found by measuring capacitance of the material to the permittivity of free space ($\in_o$), that is $K=\in/\in_o$.

Examples of low-K dielectric materials include nanoporous silica, hydrogensilsesquioxanes, teflon-AF (Polytetrafluoethylene), Silicon Oxyflouride and the like. It is noted that above-identified low-K materials are not an exhaustive list of low-K materials and other low-K materials may be available.

Figure 9B:
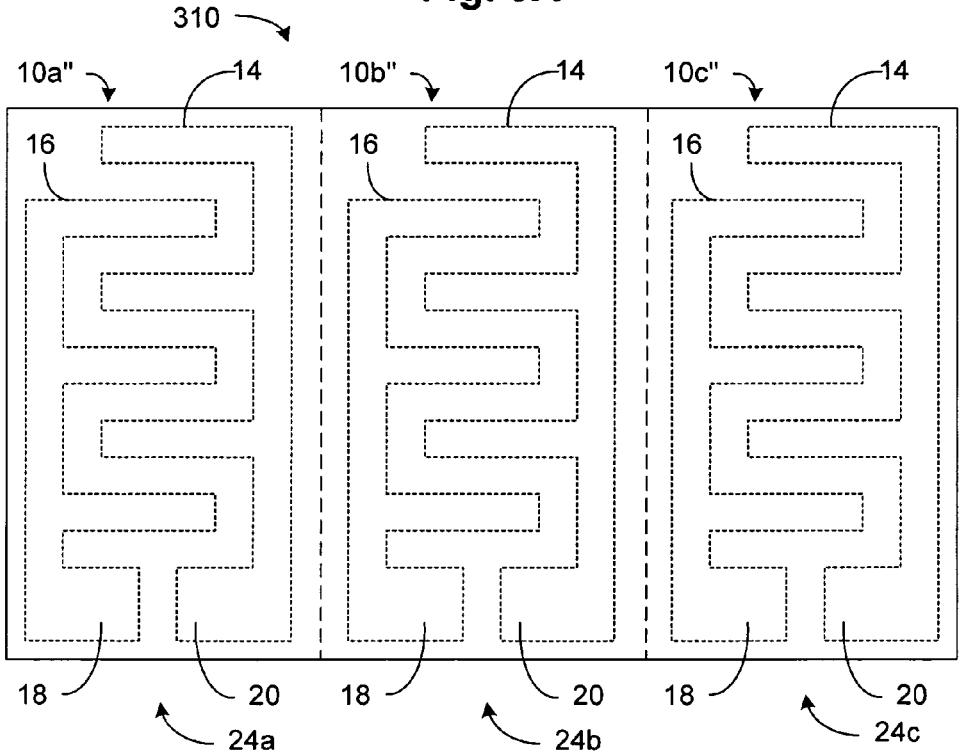
FIG. 9B is a top view of an alternative embodiment of the invention, wherein an array of MEMS-based sensors are selective to detect particular contaminants, wherein the selective layer is formed over the electrodes and the substrate.

In an alternative embodiment of FIG. 9B, one or more of the sensors 10a", 10b", 10c" in the sensor array 210, 310 may be covered with an insulating film or layer, as illustrated in FIG. 2C, to provide non-particulate contamination information, such as the water content of the fluid and/or fluid oxidation for analysis. Again, each insulating film 24a, 24b, 24c is chosen in order to provide a surface to which a fluid containing a contaminant of interest would preferentially adhere, thereby providing a stronger capacitive measurement of the presence of the particular contaminant of interest within the fluid. For example, an insulating film comprised of glass would be particularly sensitive to water within the fluid, while an insulating film comprised of silicon nitride would be particularly sensitive to soot and oxidation within the fluid.

Figure 9C:
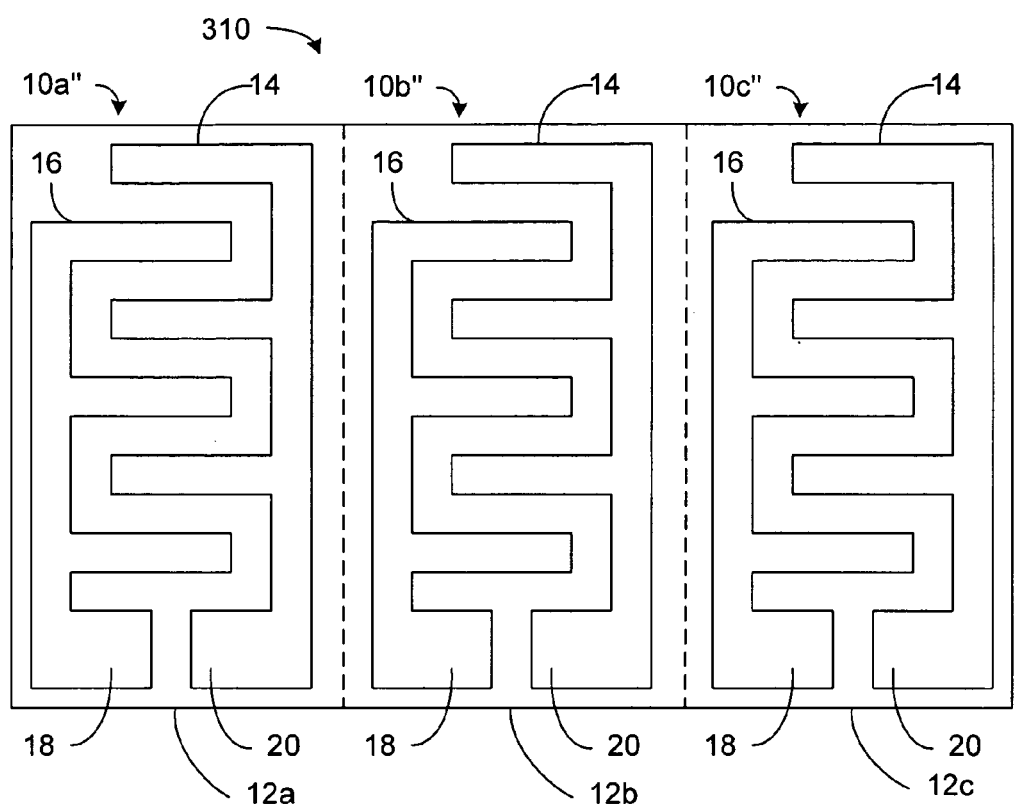
FIG. 9C is a top view of an alternative embodiment of the invention, wherein an array of MEMS-based sensors are selective to detect particular contaminants, wherein each substrate is formed of a different selective material.

In yet another alternative embodiment shown in FIG. 9C, each sensor is formed on a substrate 12a, 12b, 12c, of different material, which is selective of or otherwise sensitive to a particular contaminant being detected. In this embodiment, each sensor substrate 12a, 12b, 12c, may be mounted to a common base structure such that the sensors are disposed in proximity to one another. For example, a substrate comprised of glass would be particularly sensitive to water within the fluid, while a substrate comprised of silicon nitride would be particularly sensitive to soot and oxidation within the fluid.

Figure 10:
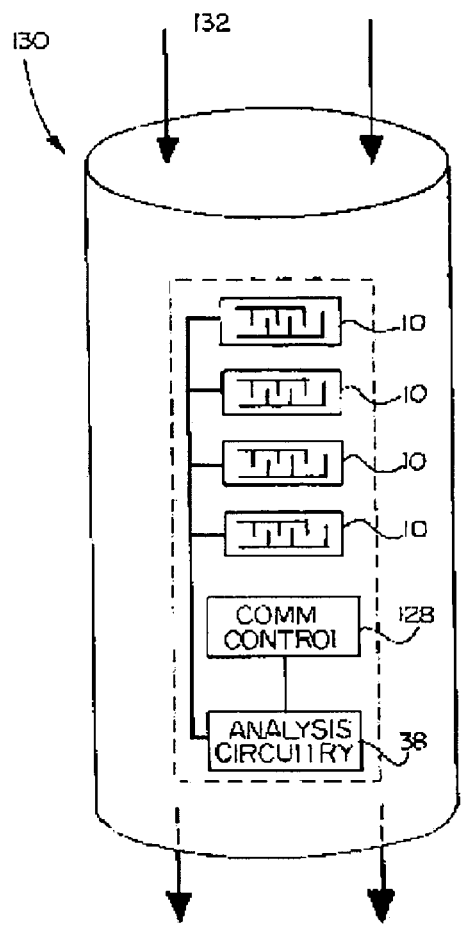
FIG. 10 is a perspective view of an in-line fluid analyzer having an array of MEMS-based sensors in a lubricant fluid flow path having both circuitry for analyzing the impedance and communicating the results to other circuitry.

FIG. 10 is a perspective view of the sensor system 130 in an in-line configuration in which the sensors 10 themselves are in a fluid flow path 132 of a machine. As discussed supra, the sensor 10 senses the fluid impedance and transmits this data to the analysis circuit 38, which analyzes and/or processes the data to arrive at a fluid contamination determination. This result may then be communicated either visually to a user who is taking a fluid contamination reading via a display (not shown) or may alternatively communicate the result to a central data collection station (not shown) via the communications control circuit 128 which is operable to transmit data, preferably via an RF signal, to the data collection station.

Figure 11:
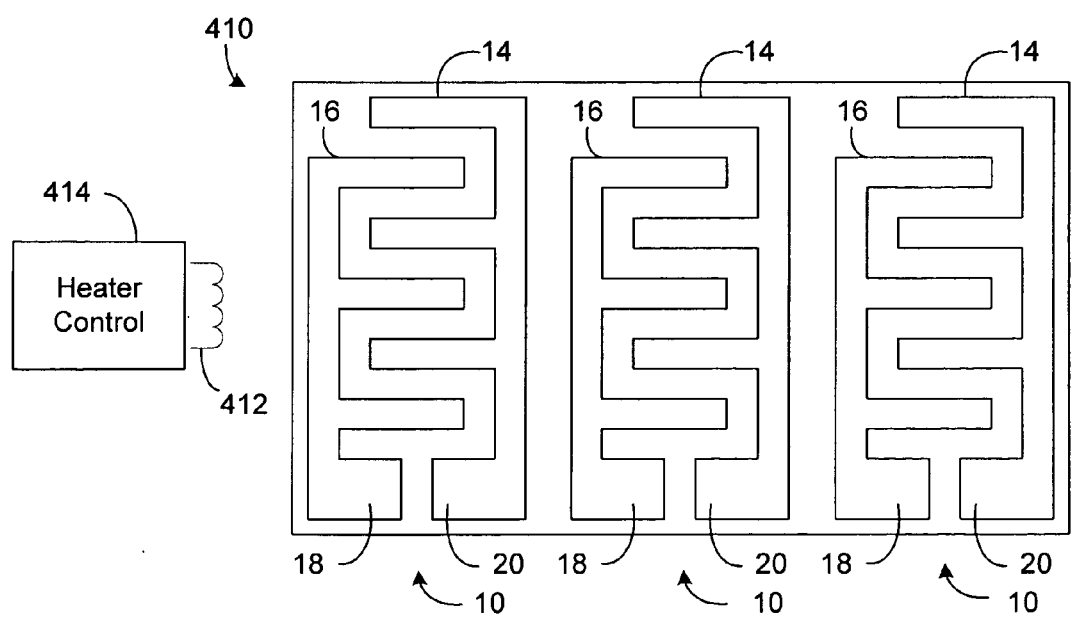
FIG. 11 is a top view of an alternative embodiment of the invention, wherein a local heater is employed to generate a temperature gradient.

With reference now to FIG. 11, a sensor system 410 in accordance with an alternative embodiment is illustrated. The system includes one or more sensors 10 disposed adjacent a local heater 412, which is controlled by a heater control 414. A local heater, as used herein, refers to a heater that is within about 5 to about 1000 microns from the sensor. The actual location of the heater with respect to the sensor is not critical, and the heater need only cause a change in temperature of the fluid so a temperature slope can be determined. The sensor system 410 performs impedance measurements on a fluid sample as the fluid is run through a temperature gradient. In one embodiment, the sensor system 410 is integrated into a probe assembly, such as is illustrated in FIGS. 3A-3C. Alternatively, the probe system 410 is embodied in an in-line configuration, such as is illustrated in FIG. 10. Because the rate at which the sensed impedance changes with temperature (temperature slope) is altered by contamination of the fluid, the change in slope can be used as an indication of fluid condition. It is to be appreciated that this embodiment of the invention may be employed in conjunction with a single sensor system as well as a multi-sensor array.

Figure 12:
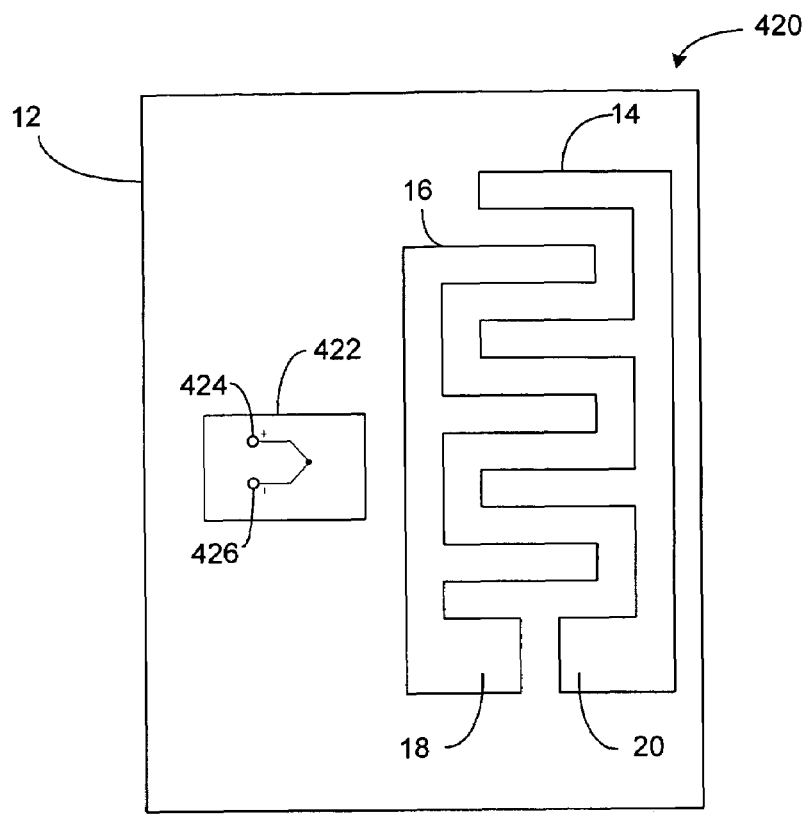
FIG. 12 is a top view of an alternative embodiment of the invention, wherein the MEMS based sensor includes a temperature sensor.

Referring now to FIG. 12, an alternative embodiment of the sensor 420 is illustrated. The sensor 420 is similar to the sensor 10, 22, 23 shown in FIGS. 2A-2C, and includes electrodes 14,16 located along a horizontal plane on the substrate 12. When a lubricant fluid sample contacts the sensor 10, it rests between and above the electrodes 14 and 16, thereby affecting the dielectric constant therebetween. Accordingly, the presence of contaminants within the fluid results in different impedance readings of the sensor at its leads (bond pads 18 and 20). Bond pads 18, 20 provide a connection point for coupling to discrete instrumentation or circuits integrated with the substrate. Additionally, the sensor 420 includes a temperature sensor 422, such as, for example, a thermocouple, a thermistor, or a Resistance Temperature Detector (RTD). Terminals 424, 426 provide a connection means for connecting the temperature sensor 422 to a monitoring device, such as the analysis circuitry 38 (FIG. 3A), for example. As will be appreciated, the number of terminals required for the temperature sensor 422 depends on the type of temperature sensor implemented, e.g., two terminals for a thermocouple, three terminals for a 3-wire RTD, etc. Alternatively, the temperature data from the temperature sensor 422 and fluid data from the sensor may be transmitted to the analysis circuitry 38 wirelessly or through a data communications link. The temperature sensor 422 provides a temperature measurement of the fluid that is in contact with the sensor 420. The temperature measurement can be used by the analysis circuitry to improve the accuracy of the analysis of the fluid, e.g., by compensating the impedance measurement of the fluid based on the temperature of the fluid.

For example, correction factors can be applied to the data obtained by the sensor 420 based on the temperature of the fluid. It may be known that the sensor 420 produces a first set of data for a fluid in a first temperature range, and a second set of data, which is different from the first set of data, in a second temperature range. In each case the fluid is identical (except for temperature), yet different test data is obtained. To compensate for this difference, a correction factor can be applied to the measured data based on the measured temperature of the fluid. It should be appreciated that the correction factor can be applied by the analysis circuitry 38 or by the temperature sensor 422 itself. Alternatively, temperature data obtained from the temperature sensor 422 can be used for monitoring the fluid temperature, thereby eliminating the need for a separate temperature sensor.

With reference now to FIG. 13, another embodiment of the sensor is illustrated. The sensor 430 again is similar to the sensor of FIGS. 2A-2C, and includes electrodes 14, 16 located along a horizontal plane on the substrate 12. Bond pads 18, 20 provide a connection point for coupling to discrete instrumentation or circuits integrated with the substrate, as described previously. Additionally, the sensor 430 includes a non-volatile memory module 432, such as an EEPROM. The non-volatile memory module 432 is operatively coupled to the sensor to receive data, such as sensor data, temperature data, etc. Additionally, the non-volatile memory module is operatively coupled to a memory controller (not shown). Memory controllers are well known and therefore will not be discussed in detail. Briefly, the memory controller coordinates the data routed to the non-volatile memory module 432 and the data retrieved from the non-volatile memory module. Additionally, the memory controller instructs the non-volatile memory module to store and/or to retrieve data to/from non-volatile memory.

The non-volatile memory module 432 can store and/or retrieve data pertaining to the sensor, e.g., calibration data, date of manufacture, serial number, sensor type etc., customer data, e.g., customer name, location, etc., or application data, e.g., location of the sensor, last maintenance date of the sensor, selected reference fluid (e.g., reference oil), operating time, minimum and maximum operating temperature, minimum and maximum fluid measurements (e.g., impedance, temperature), etc. As will be appreciated, numerous other types of data can be stored in the non-volatile memory module 432 as required. Additionally, the temperature sensor 422 of the sensor 420 and the non-volatile memory module 432 of the sensor 430 can be combined in a single sensor, thereby providing both memory storage/retrieval functions and temperature monitoring functions on a single sensor.

Figure 14:
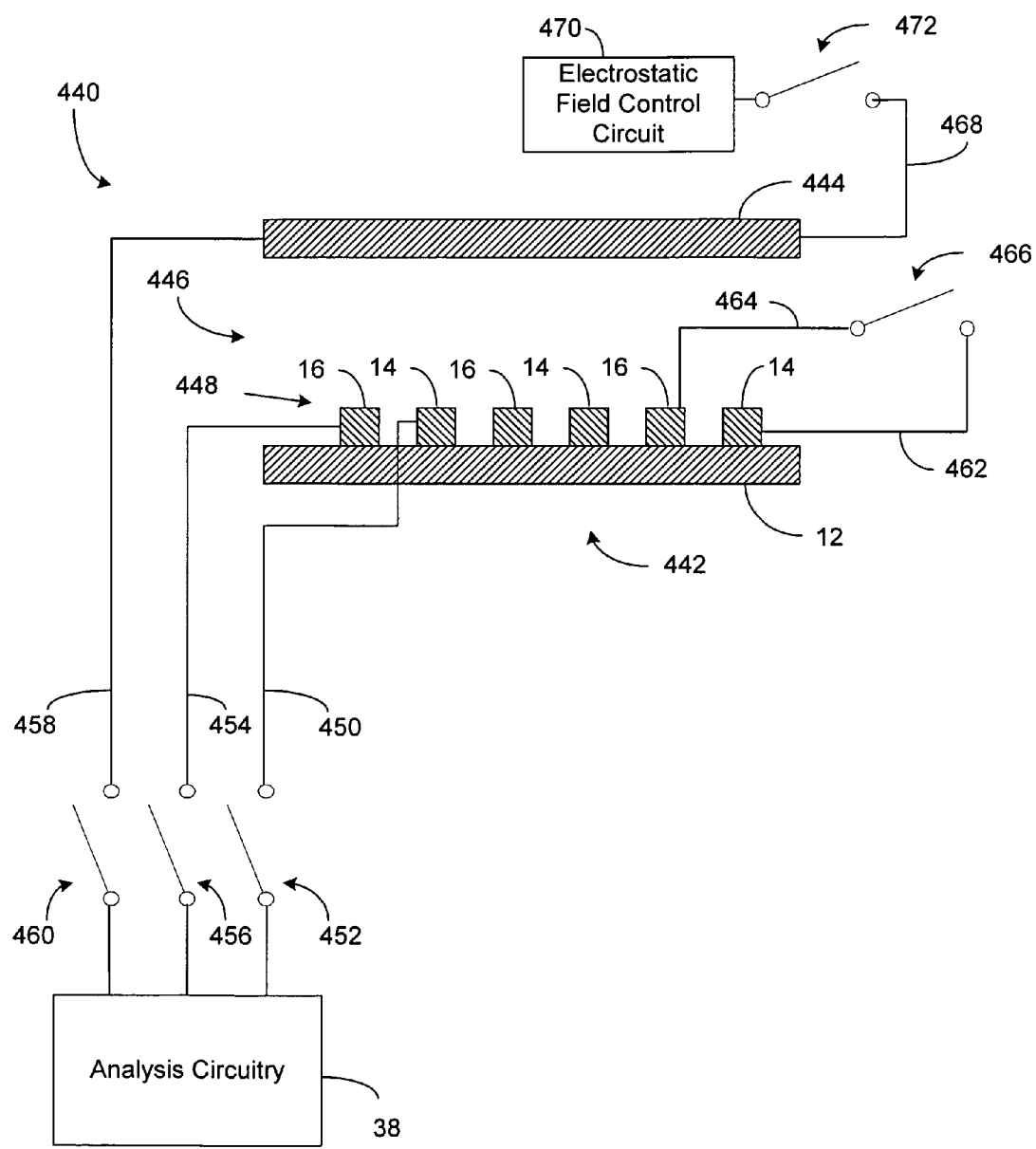
FIG. 14 is a side view of an alternative embodiment of the invention, wherein the sensor includes a MEMS based sensor and a plate electrode.

With reference to FIG. 14, another embodiment of the sensor is illustrated. The sensor 440 includes a MEMS based sensor 442 as described in any one of the previously discussed embodiments. The MEMS based sensor 442 includes electrodes 14, 16 located along a horizontal plane on the substrate 12. Bond pads (not shown) provide a connection point for coupling to discrete instrumentation or circuits integrated with the substrate. Above the MEMS sensor 442 is a plate electrode 444, which can be formed from any one of several materials, including, for example, tungsten, platinum, gold, chrome, aluminum, polysilicon, titanium, nickel, copper, silver and the like. The plate electrode 444 is generally rectangular in shape, although it should be appreciated that other shapes can be implemented without departing from the scope of the invention. The plate electrode 444 has a footprint that is about equal to a footprint of the MEMS based sensor 442. Additionally, the plate electrode 444 is generally parallel to the MEMS based sensor 442. The plate electrode can be less than 1 micron to about 10,000 microns thick, and the spacing 446 between the plate electrode and a top surface 448 of the electrodes 14, 16 can range from 50 to about 3000 microns. In one embodiment, the spacing 446 is about 1000 microns.

A first connector 450 couples the first electrode 14 to analysis circuitry 38 via a first switch 452. A second connector 454 couples the second electrode 16 to the analysis circuitry 38 via a second switch 456. A third connector 458 couples the plate electrode 444 to the analysis circuitry 38 via a third switch 460. A fourth connector 462 and a fifth connector 464 couple the first electrode 14 to the second electrode 16 via a fourth switch 466. Finally, a fifth connector 468 couples the plate electrode 444 to an electrostatic field control circuit 470 via a fifth switch 472.

As will be appreciated, the above described switches can be MEMS based switches or any other suitable switch used in low power signal systems. Additionally, connections for operating the switches are not shown. Such connections, however, would be obvious to one skilled in the art and therefore are omitted for sake of brevity. The switches can be located remote from the sensor 440, e.g., in or near the analysis circuitry 38, or integrated on the sensor 440, e.g., on the substrate 12 of the MEMS based switch 442. Based on the switch settings, the sensor 440 can operate in anyone of several modes.

In a first mode, the first switch 452 and the second switch 456 are closed, while the third switch 460 and the fourth switch 466 are open. In this mode of operation, the sensor 440 behaves as the sensors previously described herein, i.e., the sensor analyzes the fluid between and above the electrodes 14, 16 within its field of view. The sensor 440 is immersed in a fluid and a measurement is made by the analysis circuitry 38 via the first and second connectors 450, 454. The fluid surrounding the electrodes 14, 16 of the sensor 440 acts as a dielectric between the electrodes 14, 16 thereby impacting the impedance of the sensor. The analysis circuitry 38 determines the level of fluid contamination based upon either a comparison with a known clean fluid sample or with an expected or reference value.

In a second mode, the first switch 452 and the third switch 460 are closed, and the second switch 456 and the fourth switch 466 are open. In this configuration the sensor 440 measures the impedance of the bulk fluid between the first electrode 14 and the plate electrode 444. The first electrode 14 and the plate electrode 444 form the respective plates of a parallel plate capacitor, and the fluid between the plates forms the dielectric material. The analysis circuitry 38 determines the level of fluid contamination based upon either a comparison with a known clean fluid sample or with an expected or reference value.

In a third mode, the second switch 456 and the third switch 460 are closed, and the first switch 452 and the fourth switch 466 are open. In this configuration the sensor 440 measures the impedance of the bulk fluid between the second electrode 16 and the plate electrode 444. The second electrode 16 and the plate electrode 444 form the respective plates of a parallel plate capacitor, and the fluid between the plates forms the dielectric material. The analysis circuitry 38 determines the level of fluid contamination based upon either a comparison with a known clean fluid sample or with an expected or reference value.

In a fourth mode, the first switch 452, the third switch 460 and the fourth switch 466 are closed, and the second switch 456 is open. In this configuration the sensor 440 measures the impedance of the bulk fluid between the combination of the first electrode 14 and the second electrode 16 and the plate electrode 444. The first electrode 14 and the second electrode 16 form a first plate of a parallel plate capacitor, and the plate electrode 444 forms the second plate of a parallel plate capacitor. The fluid between the two plates forms the dielectric material. The analysis circuitry 38 determines the level of fluid contamination based upon either a comparison with a known clean fluid sample or with an expected or reference value. It is noted that the same configuration can be obtained by opening the first switch 452 and closing the second, third and fourth switches 456, 460, 466.

In a fifth mode, the first switch 452, the second switch 456 and the fifth switch 472 are closed and the third switch 460 and the fourth switch 466 are open. The sensor 440 operates in the following manner. After a magnetic field source (not shown) is deactivated, particulates are preferably washed away due to fluid flow. There are frequently, however, particulates that contain a residual static charge large enough to remain stuck to one of the electrodes 14 and 16 despite the fluid flow over the electrodes. The electrostatic field control circuit 470 then applies a voltage to the plate electrode 444 such that an electrostatic field is generated that is sufficiently large such that particulates are dislodged and washed away by the fluid flow. In this manner, fluid contamination accuracy is improved by eliminating the chance of residual particulates from previous fluid sample measurements interfering with subsequent fluid measurements by washing performed periodically via the electrostatic control circuit 470 and the plate electrode 444.

Figure 15:
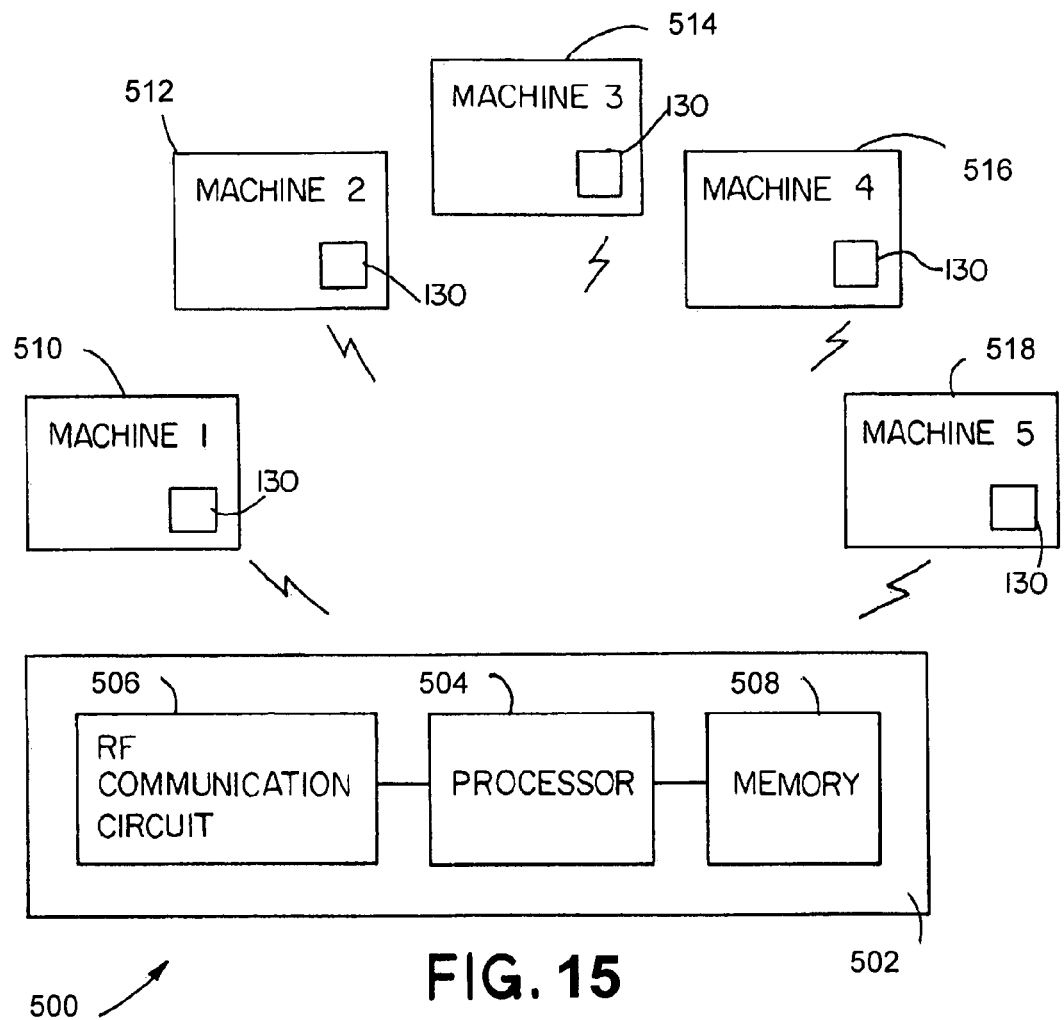
FIG. 15 is a block, system level diagram illustrating an environmental view of the invention, wherein a plurality of machines contain MEMS-based sensors for sensing fluid contamination and circuitry for communicating the results to a central data analysis and storage site.

FIG. 15 is a system level diagram, which illustrates a dynamic fluid contamination analysis system 500. System 500 includes a central data collection, processing and storage unit 502, which contains a processor 504, an RF communications circuit 506 and a memory 508. The central data collection unit 502 may also include an I/O port, an input peripheral device and a display for interacting with a user. The system 500 includes a plurality of machines 510, 512, 514, 516 and 518 which operate in a factory setting and utilize fluids of lubricant and cooling purposes. Each machine contains a sensor system 130 (as illustrated in FIG. 10, for example) that performs in an in-line configuration. Periodically, as dictated by the processor 504 and RF communications circuit 506, the sensor systems 130 are instructed to measure the fluid impedance of the fluid in their respective machines. Each sensor system 130 then communicates its present fluid impedance to the processor 504 via its communications control circuit 128. The processor 504 then makes a fluid contamination determination, stores it in the memory 508 for trending purposes and indicates the determination to monitoring personnel if the fluid contamination level exceeds a predetermined threshold. In this manner, the fluid contamination analysis system 500 monitors a plurality of machines without requiring a user to go from machine to machine taking fluid samples and interfering with the machine operation. In addition, since the sensor arrays of the present invention are small, they may serve in in-line configurations without interfering with machine operation.

Figure 16:
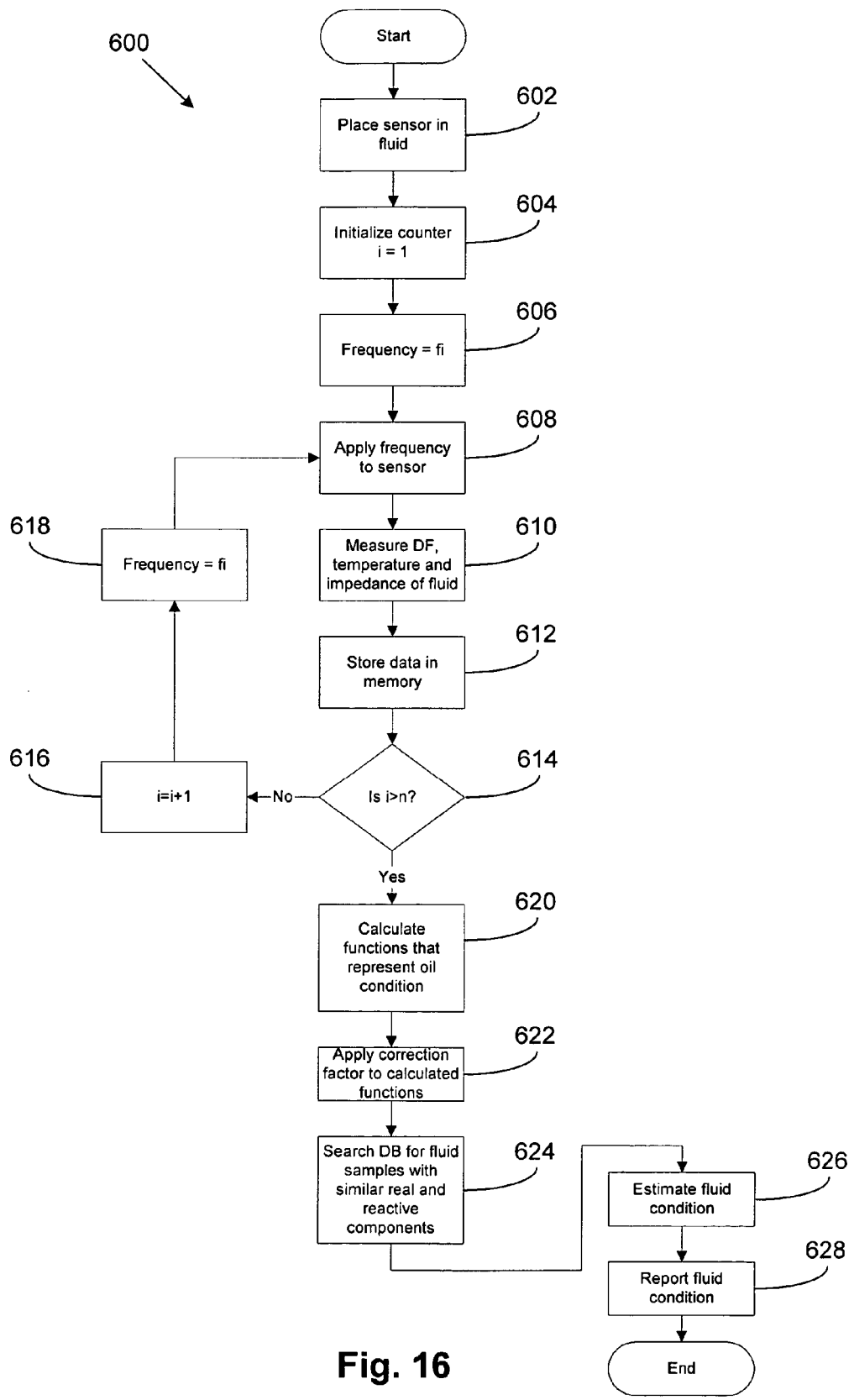
FIG. 16 is a flow diagram illustrating an exemplary method of estimating the quality of a fluid in accordance with an embodiment of the present invention.

With reference to FIG. 16, a flow diagram of an example technique, or process 600 of determining the quality of a fluid in accordance with the present invention is illustrated. The process 600 can be thought of as depicting steps in a method. The flow diagram includes a number of process blocks arranged in a particular order. As should be appreciated, many alternatives and equivalents to the illustrated process 600 may exist and such alternatives and equivalents are intended to fall within the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

As will be described more fully below, the method includes immersing a sensor into a fluid and measuring the impedance of the sensor and fluid. Based on the measured impedance, the quality of the fluid is estimated.

The method will be described in conjunction with the analysis circuitry 38 previously discussed herein. In the exemplary embodiment, the analysis circuitry is the computer 500 (FIG. 15) executing program instructions that carry out the steps of the method. It should be appreciated that the particular vehicle used to implement the method is not germane to the invention, and other forms of the analysis circuitry are contemplated. For example, the analysis circuitry could be configured as a group of discrete components interconnected together to form a logical circuit.

The sensor of the present invention can be modeled as a resistor having a resistance R connected in parallel with a capacitor having a capacitance C. Thus, the sensor includes both real and reactive components.

Another factor for consideration is the dissipation factor (DF). DF represents one form of heat-producing losses within a capacitor. DF and "loss tangent" are largely equivalent terms describing capacitor dielectric losses. DF refers specifically to losses encountered at low frequencies. At high frequencies, capacitor dielectric losses are described in terms of loss tangent (tan $\delta$). The higher the loss tangent, the greater the capacitor's equivalent series resistance (ESR) to signal power.

For small and moderate capacitor values, losses within the capacitor occur primarily in the dielectric, the medium for the energy transfer and storage. The dielectric loss angle, $\delta$, is the difference between (theta) and 90°. The name "loss tangent" simply indicates that tan $\delta$ goes to zero as the losses go to zero. Note that the dielectric's DF is also the tangent of the dielectric loss angle. These terms are used interchangeably in the art.

The actual values of R and C for the sensor model as well as the DF are dependent on the sensor itself as well as on the fluid the sensor is measuring. A clean or new fluid will produce values of R, C and DF that are distinct from values of R, C and DF produced by a contaminated or used fluid. Based on the measured values of R, C, and DF, the analysis circuitry can estimate the remaining life of the fluid, the particular type of contamination in the fluid, e.g., water, metal, soot, oxidation, additive depletion, etc., and the relative amounts of the particular type of contamination in the fluid.

Beginning at step 602, a sensor in accordance with the present invention is immersed in a fluid, such as oil from an internal combustion engine, for example. At step 604, the processor 504 initializes a counter, and at step 606 the processor selects an initial frequency f1. The selected frequency f1 can range between 0.1 Hz and 10 MHz, and preferably is at an optimum frequency for the application. According to one embodiment, f1 is between about 100 Hz and 20 KHz. The processor 504 applies the selected frequency to the bond pads 16, 18 of the sensor at step 608, and the temperature and impedance of the sensor/fluid are measured by the processor.

Moving to step 612, the processor 504 stores the measured temperature and impedance in memory 508 for use in later steps. At step 614, the processor checks the counter to determine if another iteration is required. If the counter is less than or equal to n, then at step 616 the processor 504 increments the counter, and at step 618 the processor selects a second test where electrical conditions may be changed in frequency, voltage, time duration or not changed as required by the test protocol for the application. For example, the frequency f2 can be higher, lower or equal to the frequency f1. Preferably, the frequency f2 is about 10 times the frequency f1 of the previous iteration. After selecting the second frequency, the processor 504 moves back to step 608, and the process is repeated for n tests as required by the protocol for that application.

Moving back to step 614, if the processor 504 determines the counter is greater than n, then at step 620 the processor retrieves the measured data from memory 508. At step 620, the processor calculates functions that best represent the oil conditions of concern, e.g., the impedance at each frequency. Threshold values for the functions will be determined with used fluids with known levels of contamination and/or depletion. Processor 504 will generate a report of the test point, date/time, multiple test functional values for the test point, threshold functional values and temperature, for example.

For example, and as was noted previously, the sensor can be modeled as a resistor connected in parallel to a capacitor. The impedance can be measured by applying a sine wave signal of a given frequency and amplitude to the sensor and comparing the input signal to the output signal with respect to amplitude and phase shift (phase angle). From this information, and using the parallel R-C (resistor-capacitor) model of the sensor, the impedance is resolved into real and reactive components.

Moving to step 622, once the impedance is resolved into its real and reactive components, a correction factor is applied to the complex impedance. The correction factor is based on the measured temperature of the sample fluid during the impedance measurement relative to the measured temperature of a reference fluid during its impedance measurement. The correction factor can be a simple fraction, an equation describing the change in impedance as temperature varies, or a lookup table containing the impedance of a stable fluid at various temperatures. According to one embodiment, temperature compensation factors are generated for a particular reference fluid type after all measurements of the reference fluid have been made at various temperatures.

As was discussed previously, impedance measurements of certain fluids can be affected by the temperature of the fluid. Impedances may increase, decrease or remain unchanged throughout a temperature range. Due to the operating characteristics of a particular machine, it may not be feasible to obtain an impedance measurement of a sample fluid at the same or similar temperature as an impedance measurement of a reference fluid. In such situations, a correction of the measured impedance of the sample fluid provides increased accuracy of the impedance measurement and, thus, increased accuracy in the estimate of the condition of the fluid. The correction factor for a given fluid can be stored in memory, such as a database, which is discussed in more detail below.

Now that a corrected value of the complex impedance has been calculated, the processor at step 624 retrieves reference fluid data from memory (e.g., data stored in a reference database on a storage medium, such as a hard drive of a computer). Referring briefly to FIG. 17, an exemplary database structure 700 that can be used to construct the reference database is illustrated. The database structure 700 includes a reference name entry 702, which is a listing of fluid names that may be used in a particular machine or process, e.g., 80 weight gear lube, Brand X 10W-40 motor oil, etc. A real component of impedance entry 704 stores the real component of impedance for the particular reference fluid, and a reactive component impedance entry 706 stores the reactive component of impedance for the particular reference fluid. A reference temperature entry 708 stores the temperature of the reference fluid during its impedance measurement, and a temperature compensation entry 710 stores the correction factor for the particular fluid. Additionally, a DF entry 712 stores the dissipation factor for the fluid and, finally, a fluid property entry 714 provides information relating to the characteristics of the particular fluid. For example, the condition of the reference fluid (e.g., new, used, etc.), the type of contaminants in the fluid (e.g., soot, water, fuel, etc.) and/or the amount of contaminant in the fluid (e.g., 1% fuel) is entered in the fluid property entry 714.

As will be appreciated, multiple columns for fluid property can be included in the database structure 700 depending on the requirements of the system. For example, a first fluid property entry can be dedicated to the age or remaining life of the fluid, a second fluid property entry can be dedicated to the type of contaminant in the fluid, and a third fluid property entry can be dedicated to the amount of the contaminant in the fluid. Additionally, the impedance may be expressed in other terms as described previously, e.g., terms other than real/reactive components and DF.

Each reference fluid is entered into the reference database along with its respective properties as in the above described entries. For example, a first fluid name entry 702 may be Brand X 10W-30 motor oil, and is entered in a first row 720 of the database. Corresponding fluid properties, real component of impedance, reactive component of impedance, reference temperature, correction factor, and DF also are stored in the first row under their respective columns. A second fluid name may be the same fluid, e.g., Brand X 10W-30 motor oil, and is entered in a second row 722 of the reference database, along with its corresponding fluid properties, real component of impedance, reactive components of impedance, reference temperature, correction factor and DF. As should be apparent, the second entry will have a different fluid property, and thus different values for the real component of impedance, the reactive component of impedance, or the DF. The reference temperature entry 708 may or may not be the same, depending on the temperature of the second reference fluid during its impedance measurement. The temperature compensation entry 710 is the same for reference fluids of the same type. Further entries can be made for the same type of fluid and/or for different types of fluid, as needed. In one embodiment, the reference database includes a single type of reference fluid, and numerous entries for the reference fluid at various levels of contamination and/or various type of contaminants.

In operation, the processor searches and retrieves from the database 700 fluid name entries 702 that match the fluid sample being tested. From the list of matching fluid names, the processor searches the real component of impedance 704, the reactive component of impedance 706, and the DF 712 for values that match or are within a specified range of the calculated real component of impedance, the calculated reactive component of impedance and the calculated DF for the sample fluid. At step 626, the processor 504 estimates the sample fluid to have the same fluid properties as a reference fluid of the same type with the same or similar DF, real component of impedance and reactive component of impedance. At step 628, the status of the fluid is reported to a user via an screen, e.g., a computer monitor, or via a status indicator, for example.

The various features of the present invention may be utilized in a variety of applications, configurations and packages. For example, the aspects of each embodiment can be mixed and matched to create alternative embodiments. Each variation is contemplated as falling within the scope of the present invention. Additionally, the sensors may be potted or secured in a DIP (dual in-line package) for easy insertion and replacement. Furthermore, the number of iterations at various frequencies may be increased as required.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A fluid contamination analyzer, comprising: a reference MEMS-based sensor disposed within a reference housing, said reference housing containing a substantially contaminant-free volume of the fluid being analyzed; and a plurality of sample MEMS-based sensors disposed adjacent the reference housing within a fluid;
    wherein the reference sensor and the sample sensors further comprise: a substrate; a plurality of electrodes formed over the substrate; and a contaminant selective layer disposed adjacent at least one of (i) the electrodes or (ii) the substrate, said layer being selective to attract a predetermined contaminant within the fluid; wherein when a fluid contacts the sensor an impedance of the fluid may be determined using the electrodes of the sensor, thereby providing an indication of fluid contamination;
    a plate electrode disposed over the reference sensor and at least one sample sensor of the plurality of sample sensors, wherein when a fluid is disposed between the plate electrode and the MEMS based sensors an impedance of the fluid is determined using the plate electrode and at least one electrode of the MEMS based sensors;
    associated with each sensor, a first switch operatively coupled to a first electrode of the plurality of electrodes; a second switch operatively coupled to a second electrode of the plurality of electrodes; a third switch operatively coupled to the plate electrode; and a fourth switch operatively coupled to the first electrode and the second electrode
    wherein the plurality of switches selectively configure the fluid contamination analyzer to measure an impedance between the plate electrode and at least one electrode of the at least one MEMS based sensor or between and adjacent to the electrodes of the MEMS based sensor.

2. The fluid contamination analyzer according to claim 1, wherein the contaminant selective layer comprises a top layer disposed over the electrodes.

3. The fluid contamination analyzer according to claim 2, wherein the contaminant selective layer is a low-K dielectric material.

4. The fluid contamination analyzer according to claim 3, wherein the low-K dielectric material is chosen from the group consisting of nanopourous silica, hydrogensilsesquioxanes, teflon-AF (Polytetrafluoethylene) and Silicon Oxyflouride.

5. The fluid contamination analyzer according to claim 1, wherein the electrodes are formed from the group consisting of tungsten, platinum, gold, chrome, aluminum, polysilicon, titanium, nickel, copper and silver.

6. The fluid contamination analyzer according to claim 1, wherein the plurality of electrodes are interdigitated.

7. The fluid contamination analyzer according to claim 6, wherein a spacing between adjacent electrodes is between about 1 micron to about 250 microns.

8. The fluid contamination analyzer according to claim 6, wherein a spacing between adjacent electrodes is less than 1 micron.

9. The fluid contamination analyzer according to claim 1, further comprising at least one temperature sensor for measuring a temperature of the fluid in contact with the reference sensor and/or sample sensors.

10. The fluid contamination analyzer according to claim 9, wherein the temperature of the fluid is used to compensate the impedance measurement of the fluid.

11. The fluid contamination analyzer according to claim 9, wherein the temperature sensor is selected from the group consisting of a thermocouple, a thermistor and a resistance temperature detector (RTD).

12. The fluid contamination analyzer according to claim 9, wherein temperature data and/or sensor data is communicated to a remote monitoring device through a communications link.

13. The fluid contamination analyzer according to claim 12, wherein the communications link is a wireless communications link.

14. The fluid contamination analyzer according to claim 1, further comprising a non-volatile memory module for storing data.

15. The fluid contamination analyzer of according to claim 14, wherein the data stored in the non-volatile memory module is at least one of a customer name, a serial number of the sensor, a manufacture date of the sensor, a calibration factor of the sensor, a temperature of the fluid, a sensor type, a location of sensor, a maintenance date of the sensor, a selected reference oil, or an impedance of the fluid.

16. The fluid contamination analyzer according to claim 14, wherein the non-volatile memory module is an electrically erasable programmable read only memory module (EEPROM).

17. The fluid contamination analyzer according to claim 1, further comprising a temperature sensor for measuring a temperature of the fluid in contact with the sensor and a non-volatile memory module for storing data.

18. The fluid contamination analyzer according to claim 1, wherein the plurality of switches are MEMS switches.

19. The fluid contamination analyzer according to claim 1, wherein the plurality of switches are formed on the substrate of the MEMS based sensor.

20. The fluid contamination analyzer according to claim 1, wherein the plate electrode and the plurality of electrodes are formed from the group consisting of tungsten, platinum, gold, chrome, aluminum, polysilicon, titanium, nickel, copper and silver.

21. The fluid contamination analyzer according to claim 1, wherein the plate electrode is about 1 micron to about 10,000 microns thick.

22. The fluid contamination analyzer according to claim 1, wherein the plate electrode is substantially parallel to a top surface of the at least one MEMS based sensor.

23. The fluid contamination analyzer of claim 1, wherein the substrate is at least one of a glass substrate or a quartz substrate.

24. The fluid contamination analyzer of claim 1, wherein the plurality of electrodes have a width between about 1 micron to about 50 microns.

25. The fluid contamination analyzer of claim 1, further comprising a selectively activatable electromagnet in proximity to the sample sensors, wherein the magnet may be activated and deactivated in response to control signals and provides a magnet gradient across the sample sensors, wherein the magnet gradient provides a contaminant distribution across the sample sensors.

26. A method of analyzing the quality of a sample fluid, wherein the fluid acts as a dielectric on the sensor, comprising the steps of:
    immersing a sample sensor of claim 1 in the sample fluid;
    immersing a reference sensor of claim 1 in a substantially contaminant-free reference fluid, wherein the reference fluid and the sample fluid are the same type of fluid;
    measuring an impedance of the fluid near the surface of the sample sensor and the reference sensor; and
    correlating the quality of the sample fluid to the measured impedance of the sample fluid and the reference fluid.

27. The method of claim 26, wherein the step of measuring an impedance includes the step of measuring at least one of capacitance, resistance, reactance, dissipation factor, phase angle, admittance, susceptance or conductance.

* * * * *